United States Patent [19]
Sohda et al.

[11] Patent Number: 5,955,491
[45] Date of Patent: *Sep. 21, 1999

[54] METHOD FOR TREATING OSTEOPOROSIS

[75] Inventors: Takashi Sohda, Osaka; Yukio Fujisawa, Kobe; Tsuneo Yasuma; Junji Mizoguchi, both of Osaka; Masakuni Kori, Hyogo; Masayuki Takizawa, Kobe, all of Japan

[73] Assignee: Takeda Chemical Industries, Ltd., Osaka, Japan

[ * ] Notice: This patent is subject to a terminal disclaimer.

[21] Appl. No.: 08/495,352

[22] Filed: Jun. 27, 1995

Related U.S. Application Data

[62] Division of application No. 08/192,038, Feb. 4, 1994, Pat. No. 5,498,728.

[30] Foreign Application Priority Data

Feb. 19, 1993 [JP] Japan ..................................... 5-030182
Aug. 9, 1993 [JP] Japan ..................................... 5-197305

[51] Int. Cl.[6] ...................... A61K 31/405; A61K 31/195; A61K 31/41; A61K 31/435; A61K 31/495

[52] U.S. Cl. .......................... 514/415; 514/247; 514/252; 514/253; 514/256; 514/262; 514/263; 514/264; 514/307; 514/311; 514/357; 514/365; 514/372; 514/374; 514/378; 514/381; 514/383; 514/397; 514/399; 514/400; 514/405; 514/406; 514/411; 514/428; 514/432; 514/438; 514/443; 514/456; 514/464; 514/465; 544/224; 544/242; 544/264; 544/353; 546/138; 546/139; 546/336; 548/125; 548/127; 548/128; 548/131; 548/143; 548/202; 548/214; 548/235; 548/237; 548/240; 548/250; 548/255; 548/262.2; 548/335.1; 548/361.1; 548/373.1; 548/440; 548/469; 548/561; 549/23; 549/29; 549/32; 549/362

[58] Field of Search ..................................... 514/397, 399, 514/400, 415, 419, 464, 465

[56] References Cited

U.S. PATENT DOCUMENTS 5,498,728   3/1996   Sohda et al. .............................. 548/493

OTHER PUBLICATIONS

Pilbeam et al., "Inhibition by 17B Estradiol of PTH Stimulated Resorption and Prostaglandin Production in cultured Neonatial Mouse Calvariae", Biochem. and Biophys. Res. Comm., vol. 163, No. 3, pp. 1319–1324, Sep. 29, 1989.

(List continued on next page.)

*Primary Examiner*—Johann Richter
*Assistant Examiner*—Jane C. Oswecki
*Attorney, Agent, or Firm*—David G. Conlin; David S. Resnick; Dike, Bronstein, Roberts & Cushman, LLP

[57] ABSTRACT

The present invention provides a cathepsin L inhibitor containing a compound of the formula:

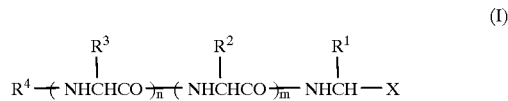

wherein $R^1$ is a hydrogen atom or an arylalkyl, heterocyclic-alkyl or lower alkyl group which may be substituted; $R^2$ and $R^3$ independently are a hydrogen atom or a hydrocarbon residue which may be substituted; $R^4$ is an alkanoyl, sulfonyl, carbonyloxy, carbamoyl or thiocarbamoyl group which may be substituted; X is formula: —CHO or —CH$_2$OB (wherein B is a hydrogen atom or a protecting group of hydroxyl group); m and n independently are an integer of 0 or 1; provided that $R^4$ is an alkanoyl group substituted by aryl, a sulfonyl group substituted by aryl having more than 9 carbon atoms or by lower alkyl, or a carbamoyl or thiocarbamoyl group which may be substituted when $R^1$ is an unsubstituted lower alkyl, arylalkyl on methylthioethyl group, $R^2$ and $R^3$ independently are a lower alkyl or arylalkyl, X is —CHO, m is 1 and n is 0 or 1, or a salt thereof.

51 Claims, 1 Drawing Sheet

OTHER PUBLICATIONS

Eriksen et al., "Evidence of Estrogen Receptors in Normal Human Osteoblast–like Cells," Science, vol. 241, pp. 84–86, Jul. 1, 1988.

Morris Notelovitz, "Estrogen Therapy and Osteoporosis: Principles & Practice," The American J. of the Medical Sciences, vol. 313, No. 1, pp. 2–12, Jan. 1, 1997.

Driguez et al., *Canadian Journal of Chemistry*, vol. 56, pp. 119–130 (1978).

Towatari et al., *FEBS Letters*, vol. 280, No. 2, pp. 311–315 (1991).

Aoyagi et al., *The Journal of Antibiotics*, vol. 22, No. 6, pp. 283–286 (1969).

Hanada et al., *Agricultural and Biological Chemistry*, vol. 42, No. 3, pp. 523–528 (1978).

Hanada et al., *Agricultural and Biological Chemistry*, vol. 42, No. 3, pp. 537–541 (1978).

Hanada et al., *Agricultural and Biological Chemistry*, vol. 42, No. 3, pp. 529–536 (1978).

Murata et al., *FEBS Letters*, vol. 280, No. 2, pp. 307–310 (1991).

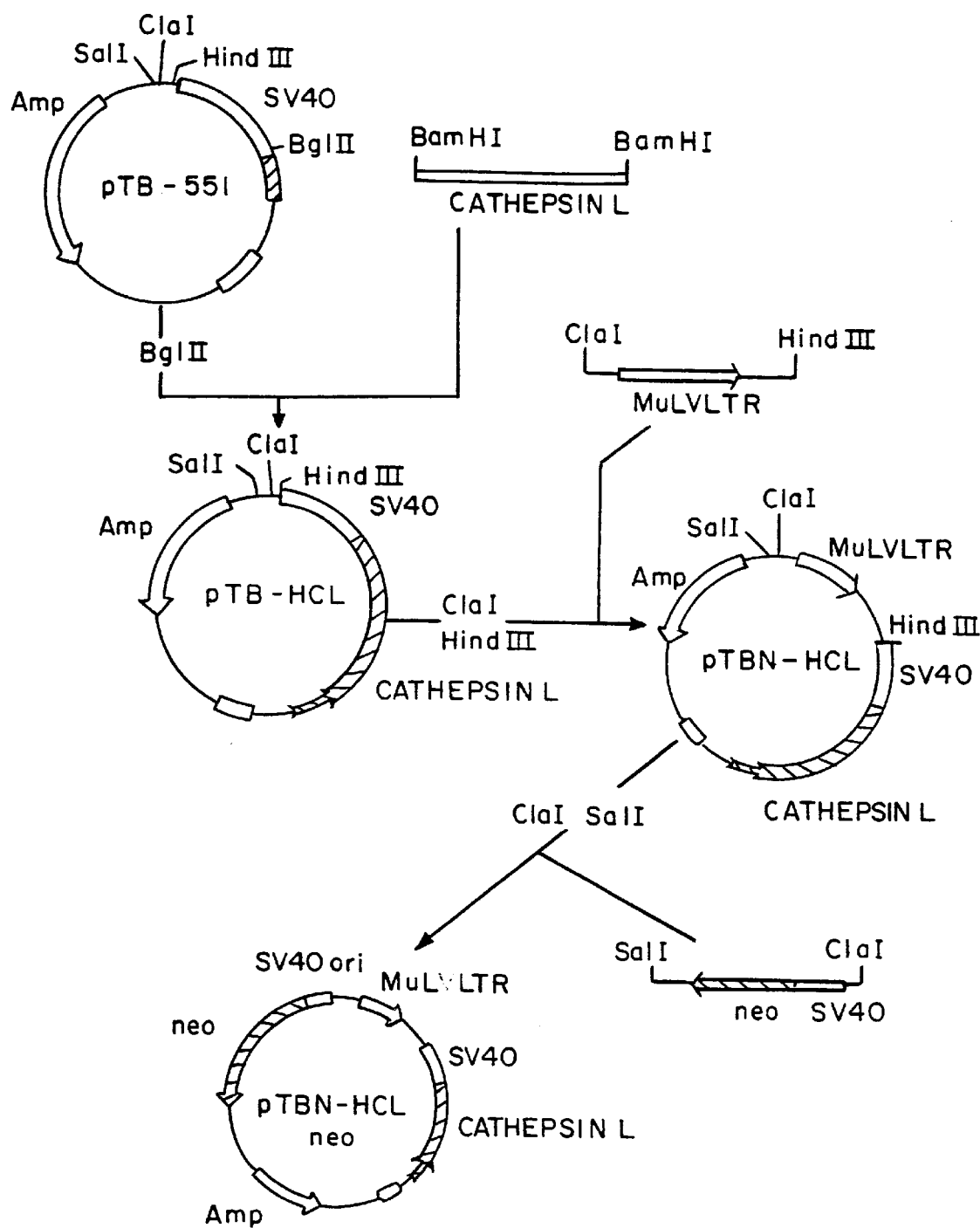
F I G. I

METHOD FOR TREATING OSTEOPOROSIS

This is a divisional of application Ser. No. 08/192,038 filed on Feb. 4, 1994 now U.S. Pat. No. 5,498,728.

FIELD OF THE INVENTION

The present invention relates to a cathepsin L inhibitor and bone resorption inhibitor containing an alcohol or aldehyde derivative, or salt thereof as an active ingredient.

BACKGROUND OF THE INVENTION

Osteoporosis is a pathologic state or disease involving some symptom or risk due to quantitative bone reduction exceeding a certain degree. Major symptoms are spinal kyphosis, fractures of dorsolumbar bones, vertebral centra, femoral necks, lower end of radius, ribs, upper end of humerus, and others. In normal bone tissue, bone breakdown occurs constantly, but there is good balance between bone formation and resorption; osteoblasts and osteoclasts play key roles in bone formation and bone resorption, respectively. Upon deterioration of this balance, bone resorption surpasses bone formation, resulting in quantitative bone reduction. Drugs suppressing bone resorption are therefore expected to serve well in preventing and treating osteoporosis. Traditionally, bone resorption-suppressing agents such as estrogens and calcitonin have been used to treat osteoporosis. However, these therapeutic agents fail to achieve satisfactory effect in some cases, due to subject limitations or uncertain efficacy. There is therefore need of a new prophylactic/therapeutic method for accentuated bone resorption.

It has recently been shown that cathepsin L, a protease secreted by osteoclasts in the process of bone resorption, is involved in the decomposition of collagen, a bone supporting protein. Epoxysuccinic acid derivatives, such as those disclosed in Japanese Patent Unexamined Publication Nos. 304074/1990, 304075/1990 and 304085/1990 appear to exhibit cathepsin L inhibitory action. However, as disclosed in the above patent publications, these epoxysuccinic acid derivatives inhibit not only cathepsin L but also other proteases.

Traditionally, leupeptin and antipain have been known to inhibit protease activity, and various compounds have been synthesized as aldehyde derivatives from amino acids. For example, acetyl-Leu-Leu-tryptophanal, acetyl-Leu-Leu-phenylalaninal etc. are disclosed as chymotrypsin inhibitors in Biochemical and Biophysical Research Communications, Vol. 49, p. 343 (1972). Peptide-derived phenylalaninal and tryptophanal derivatives are disclosed as chymotrypsin inhibitors and myodystrophy remedies in PCT Int. Appl. WO 8400365. Also, PCT Int. Appl. WO 9214696 and PCT lit. Appl. WO 9204045 disclose the anti-HIV activity of peptide-derived phenylalaninal derivatives and the CCK (cholecystokinin) antagonist activity of N-acyltryptophanal, respectively. EP-A2-0 504 938 discloses a use for prophylaxis or treatment of bone disease of peptidic aldehyde derivatives based on their hypocalcemic effect. However, these references do not disclose peptide derivatives useful in the inhibition of cathepsin L activity.

It would be desirable to have an agent that can be used to suppress bone resorption.

It would also be desirable to have an agent that is capable of inhibiting cathepsin L activity without significantly inhibiting other proteases.

It would further be desirable to have a method that can be used to readily screen and select compounds that affect bone resorption.

SUMMARY OF THE INVENTION

The present inventors sought to develop a more commonly applicable drug showing selective inhibition of cathepsin L and direct action on the bone to suppress bone resorption, and found that an alcohol and aldehyde derivative represented by the following general formula (I) shows potent cathepsin L inhibition and direct action on the bone to excellently suppress bone resorption. The inventors made further investigations based on this finding, and developed the present invention.

Accordingly, the present invention relates to:
(1) a cathepsin L inhibitor containing a compound of the formula:

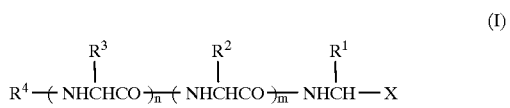

wherein $R^1$ is a hydrogen atom or an arylalkyl, heterocyclic-alkyl or lower alkyl group which may be substituted; $R^2$ and $R^3$, independently are a hydrogen atom or a hydrocarbon residue which may be substituted; $R^4$ is an alkanoyl, sulfonyl, carbonyloxy, carbamoyl or thiocarbamoyl group which may be substituted; X is formula: —CHO or —CH$_2$OB (wherein B is a hydrogen atom or a protecting group of hydroxyl group); m and n independently are an integer of 0 or 1; provided that $R^4$ is an alkanoyl group substituted by aryl, a sulfonyl group substituted by aryl having more than 9 carbon atoms or by lower alkyl or a carbamoyl or thiocarbamoyl group which may be substituted when $R^1$ is an unsubstituted lower alkyl, arylalkyl or methylthiomethyl group, $R^2$ and $R^3$ independently are a lower alkyl or arylalkyl group, X is —CHO, m is 1 and n is 0 or 1, or a salt thereof,
(2) A bone resorption inhibitor containing the compound of the formula (I) or a salt thereof,
(3) A compound of the formula (I) or a salt thereof,
(4) The compound of (3) wherein $R^1$ is an indolyl-lower alkyl,
(5) The compound of (3) wherein $R^1$ is a naphthyl-lower alkyl,
(6) The compound of (3) wherein $R^1$ is a phenyl-lower alkyl,
(7) The compound of (3) wherein $R^1$ is a hydrogen or lower alkyl,
(8) The compound of (3) wherein $R^2$ is a branched lower alkyl,
(9) The compound of (3) wherein $R^2$ is a phenyl-lower alkyl,
(10) The compound of (3) wherein $R^3$ is a branched lower alkyl,
(11) The compound of (3) wherein $R^3$ is hydrogen,
(12) The compound of (3) wherein $R^4$ is an alkanoyl, sulfonyl, carbonyloxy, carbamoyl or thiocarbamoyl group substituted by an alkyl, aryl, arylalkyl or alicyclic hydrocarbon group,
(13) The compound of (12) wherein $R^4$ is an alkanoyl group substituted by aryl, a sulfonyl group substituted by aryl having more than 9 carbon atoms or by lower alkyl or a carbamoyl or thiocarbamoyl group which may be substituted,
(14) The compound wherein X is —CHO or —CH$_2$OH,
(15) The compound of (3) wherein m is 1 and n is 1,
(16) The compound of (3) wherein m is 1 and n is 1,
(17) The compound of (3) wherein m is 1 and n is 1,
(18) The compound of (3) wherein $R^1$ is a lower alkyl which may be substituted by indolyl; $R^2$ is a lower alkyl; $R^4$ is a naphthylsulfonyl or dibenzylacetyl; X is —CHO or —CH₂OH; m is O or 1 and n is O,

(19) A method of producing the compound as defined in (3) which comprises reacting a compound of the formula:

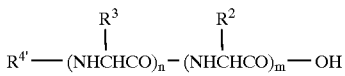

wherein R² and R³ independently are a hydrogen atom a hydrocarbon residue which may be substituted; R⁴' is an alkanoyl, sulfonyl, carbonyloxy group which may be substituted, or its reactive derivative with a compound of the formula:

wherein R¹ is a hydrogen atom or an arylalkyl, heterocyclic-alkyl or lower alkyl group which may be substituted, and if desired, subjecting to an oxidation reaction or a reaction of protecting a hydroxyl group, and

(20) A method of producing the compound as defined in (3) which comprises reacting a compound of the formula:

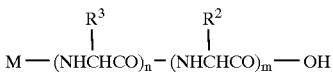

wherein R² and R³ independently are a hydrogen atom or a hydrocarbon residue which may be substituted, M is a protecting group of amino group; m and n independently are an integer of O or 1, or its reactive derivative with a compound of the formula:

wherein R¹ is a hydrogen atom or an arylalkyl, heterocyclic-alkyl or lower alkyl group, subjecting to deprotecting reaction, to acylation, sulfonylation, oxycarbonylation, carbamoylation or thiocarbamoylation reaction in this order, and if disired, subjecting to an oxidation reaction or a reaction of protecting a hydroxyl group.

The present invention further includes methods for screening and selecting compounds that affect bone resorption.

BRIEF DESCRIPTION OF THE DRAWING

FIG. 1 is a construction scheme for the plasmids obtained in Experimental Examples 4 and 5.

DESCRIPTION OF THE PREFERRED EMBODIMENTS

In the present specification, the constituent amino acids are of the L-configuration, unless otherwise stated. When shown by abbreviations, their notation is in accordance with the IUPAC (International Union of Pure and Applied Chemistry)-IUB (International Union of Biochemistry) Biochemical Nomenclature, e.g., Gly for glycine, Leu for leucine and Ee for isoleucine. Amino-protecting groups known to those skilled in the art are used. Preferable amino-protecting groups include acetyl, benzyloxycarbonyl, 4-methoxybenzyloxycarbonyl, t-butoxycarbonyl, phthalyl and formyl, with preference given to benzyloxycarbonyl or t-buthoxycarbonyl.

With respect to formula (I) above, the arylalkyl group for R¹, which may be substituted for, is exemplified by phenyl, naphthyl, anthryl, phenanthryl and acenaphthylenyl, and monocyclic or condensed polycyclic aromatic hydrocarbon groups resulting from binding of an aromatic hydrocarbon ring residue having 6 to 14 carbon atoms and a lower alkylene having 1 to 4 carbon atoms, such as benzyl, 2-phenylethyl, 3-phenylpropyl, 2-phenylpropyl, 1-phenylpropyl, α-naphthylmethyl, α-naphthylethyl, β-naphthylmethyl and β-naphthylethyl etc.

The heterocyclic alkyl group for R¹, which may be substituted for, is exemplified by those resulting from binding of an aromatic heterocyclic ring residue as exemplified below and a lower alkyl having 1 to 4 carbon atoms.

The aromatic heterocyclic ring residue is exemplified by 5- to 7-membered heterocyclic groups containing 1 atom of sulfur, nitrogen or oxygen, 5- to 6-membered heterocyclic groups containing 2 to 4 atoms of nitrogen and 5- or 6-membered aromatic heterocyclic groups containing 1 or 2 atoms of nitrogen and 1 atom of sulfur or oxygen. These aromatic heterocyclic groups may have condensed with a 6-membered ring containing 2 or fewer atoms of nitrogen, a benzene ring or a 5-membered ring containing 1 atom of sulfur. Aromatic heterocyclic groups include 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol-4-yl, tetrazol-5-yl, benzimidazol-2-yl, indol-3-yl, 1H-indazolyl, benz[b]furanyl, isobenzofuranyl, benz[b] thienyl, 1H-pyrrolo[2,3-b]pyradin-2-yl, 1H-pyrrolo[2,3-b] pyridin-6-yl, 1H-imidazo[4,5-b]pyridin-2-yl, 1H-imidazo[4, 5-c]pyridin-2-yl and 1H-imidazo[4,5-b]pyrazin-2-yl etc.

The lower alkyl group for R¹, which may be substituted for, is exemplified linear or branched C₁₆ alkyl group, such as methyl, ethyl, propyl, isopropyl, butyl, isobutyl, sec-butyl, tert-butyl, pentyl, isopentyl, neopentyl, tert-pentyl, hexyl, 4-methylpentyl, 1, 1-dimethylbutyl, 2, 2-dimethylbutyl, 3, 3-dimethylbutyl and 2-ethylbutyl etc.

The aryl group or aromatic heterocyclic ring residue in the arylalkyl group or aromatic heterocyclic alkyl group and lower alkyl group for R¹, which may be substituted for, may have 1 to 3 substituents at any positions thereon. These substituents are exemplified by aliphatic chain hydrocarbon groups, alicyclic hydrocarbon groups, aryl groups, aromatic heterocyclic groups, non-aromatic heterocyclic groups, halogen atoms, nitro groups, amino groups which may be substituted for, acyl groups which may be substituted for, hydroxyl groups which may be substituted for, thiol groups which may be substituted for and carboxyl groups which may be esterified.

Such aliphatic chain hydrocarbon groups include linear or branched aliphatic hydrocarbon groups such as alkyl groups, preferably those having 1 to 10 carbon atoms, alkenyl groups, preferably those having 2 to 10 carbon atoms, and alkynyl groups. Preferable alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl. Preferable alkenyl groups include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Preferable alkynyl groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl etc.

Such alicyclic hydrocarbon groups include saturated or unsaturated alicyclic hydrocarbons such as cycloalkyl groups, cycloalkenyl groups and cycloalkadienyl groups. Preferable cycloalkyl groups include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl and bicyclo[4.3.1]decyl. Preferable cycloalkenyl groups include 2-cyclopenten-1-yl, 3-cyclopenten-1-yl, 2-cyclohexen-1-yl and 3-cyclohexen-1-yl. Preferable cycloalkadienyl groups include 2,4-cyclopentadien-1-yl, 2,4-cyclohexadien-1-yl and 2,5-cyclohexadien-1-yl etc.

Such aryl groups are monocyclic or condensed polycyclic aromatic hydrocarbon groups, preferably phenyl, naphthyl, anthryl, phenanthryl, acenaphthylenyl and others, with preference given to phenyl, 1-naphthyl, 2-naphthyl and others.

Preferable aromatic heterocyclic groups include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1-H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl etc.

Such halogens include fluorine, chlorine, bromine and iodine, with preference given to fluorine and chlorine.

Such hydroxyl groups include the hydroxyl group and hydroxyl groups having an appropriate substituent, particularly a substituent for use as a hydroxyl-protecting group, such as alkoxy, alkenyloxy, aralkyloxy and acyloxy, as well as aryloxy. Said alkoxy is preferably an alkoxy having 1 to 10 carbon atoms (e.g., methoxy, ethoxy, propoxy, isopropoxy, butoxy, isobutoxy, sec-butoxy, tert-butoxy, pentoxy, isopentoxy, neopentoxy, hexyloxy, heptyloxy, nonyloxy, cyclobutoxy, cyclopentoxy, cyclohexyloxy). Said alkenyloxy is exemplified by those having 1 to 10 carbon atoms such as allyloxy, crotyloxy, 2-pentenyloxy, 3-hexenyloxy, 2-cyclopentenylmethoxy and 2-cyclohexenylmethoxy. Said aralkyloxy is exemplified by phenyl-$C_{1-4}$ alkyloxys (e.g., benzyloxy, phenethyloxy). Said acyloxy is preferably an alkanoyloxy having 2 to 4 carbon atoms (e.g., acetyloxy, propionyloxy, n-butyryloxy, isobutyryloxy). Said aryloxy is exemplified by phenoxy and 4-chlorophenoxy.

Such thiol groups include the thiol group and thiol groups having an appropriate substituent, particularly a substituent for use as a thiolprotecting group, such as alkylthio, aralkylthio and acylthio. Said alkylthio is preferably an alkylthio having 1 to 10 carbon atoms (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio). Said aralkylthio is exemplified by phenyl-$C_{1-4}$ alkylthios (e.g., benzylthio, phenethylthio). Said acylthio is preferably an alkanoylthio having 2 to 4 carbon atoms (e.g., acetylthio, propionylthio, n-butyrylthio, isobutyrylthio etc.).

Such amino groups include amino groups (—NH2 groups) substituted for by 1 or 2 of alkyl groups having 1 to 10 carbon atoms, alkenyl groups having 1 to 10 carbon atoms, aromatic groups and acyl groups (e.g., methylamino, dimethylamino, ethylamino, diethylamino, dibutylamino, diallylamino, cyclohexylamino, phenylamino, N-methyl-N-phenylamino, acetylamino, propionylamino, benzoylamino etc.).

Such acyl groups include formyl and groups resulting from binding of an alkyl having 1 to 10 carbon atoms, alkenyl having 1 to 10 carbon atoms or aromatic group and a carbonyl group (e.g., acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl etc.).

Such esterified carboxyl groups (carbonyloxy groups) include those resulting from binding of a carboxyl group and an alkyl group having 1 to 6 carbon atoms, such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl and hexyloxycarbonyl, those resulting from binding of a carboxyl group and an alkenyl group having 3 to 6 carbon atoms, such as allyloxycarbonyl, crotyloxycarbonyl, 2-pentenyloxycarbonyl and 3-hexenyloxycarbonyl, and those resulting from binding of a carbonyl group and an aralkyl group such as benzyloxycarbonyl and phenetyloxycarbonyl.

With respect to formula (I) above, the hydrocarbon residue for $R^2$ or $R^3$, which may be substituted for, is exemplified by arylalkyl groups which may be substituted for and aliphatic hydrocarbon groups which maybe substituted for. Such arylalkyl groups which may be substituted for include the same arylalkyl groups, which may be substituted for, as specified for $R^1$ above. Such aliphatic hydrocarbon groups which may be substituted for include linear or branched saturated aliphatic hydrocarbon residues having 1 to 8 carbon atoms, such as methyl, ethyl, propyl, isopropyl, butyl, isobutyl, sec-butyl, tert-butyl, pentyl, isopentyl, neopentyl, tert-pentyl, hexyl, isohexyl, heptyl and octyl, unsaturated aliphatic hydrocarbon residues having 2 to 8 carbon atoms, such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl, saturated alicyclic hydrocarbon residues having 3 to 7 carbon atoms, such as cyclopropyl, cyclobutyl, cyclopentyl, cyclohexyl and cycloheptyl, unsaturated alicyclic hydrocarbon residues having 5 to 7 carbon atoms, such as 1cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl, and groups which result from binding of one of the above-mentioned alicyclic hydrocarbon residues and a saturated aliphatic hydrocarbon residue and which have 4 to 9 carbon atoms, such as cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl.

The aliphatic hydrocarbon group for $R^2$ or $R^3$, which may be substituted for, may have 1 to 3 substituents at any positions thereon. These substituents are exemplified by the same halogen atoms, nitro groups, amino groups which may be substituted for, acyl groups which may be substituted for, hydroxyl groups which may be substituted for, thiol groups which may be substituted for and carboxyl groups which may be esterified, as specified as substituents on the aryl or aromatic heterocyclic residue ring in the arylalkyl group or aromatic heterocyclic alkyl group for $R^1$, which may be substituted for.

The alkanoyl group, carbonyloxy group and sulfonyl group for $R^4$ and $R^{4'}$ are represented by $—COR^5$, $—COOR^6$ and $—SO_2R^7$, respectively. The carbamoyl and thiocarbamoyl group for $R^4$ are represented by $CONHR^8$ and $—CSNHR^9$, respectively. ($R^5$, $R^6$, $R^7$, $R^8$ and $R^9$, whether identical or not, independently represent a hydrocarbon residue which may be substituted for).

The hydrocarbon residue for $R^5$ $R^6$, $R^7$, $R^8$ or $R^9$, which may be substituted for, is exemplified by aliphatic hydrocarbon groups, aromatic hydrocarbon groups and heterocyclic groups. Such aliphatic hydrocarbon groups are exemplified by the same examples as those given above for the aliphatic hydrocarbon group for $R^2$ or $R^3$, which may be substituted for. Such aromatic hydrocarbon groups are exemplified by the same examples as those given above for the aryl group in the arylalkyl group for $R^1$, $R^2$ or $R^3$, which may be substituted for. Such heterocyclic groups are exemplified by non-aromatic heterocyclic groups such as oxylanyl, azetidinyl, oxetanyl, thietanyl, pyrrolidinyl, tetrahydrofuryl, thiolanyl, piperizinyl, tetrahydropyranyl, morpholinyl, -thiomorpholinyl, piperazinyl, homopiperizinyl, pyrrolinyl and imidazolizinyl, as well as by the same examples as those given above for the aromatic heterocyclic residues on the aromatic heterocyclic alkyl group for $R^1$, which may be substituted for. These non-aromatic heterocyclic groups may be condensed with a benzene ring, a 6-membered ring containing 2 or less atoms of nitrogen or a 5-membered ring containing 1 atom of sulfur. Specifically, such condensed non-aromatic heterocyclic groups include chromanyl, isochromanyl, thiochromanyl and isothiochromanyl. The aliphatic hydrocarbon groups, aromatic hydrocarbon groups and heterocyclic groups mentioned above to exemplify the hydrocarbon residue for $R^5$, $R^6$, $R^7$, $R^8$ or $R^9$, which may be substituted for, may have 1 to 3 substituents at any positions thereon. Such substituents are exemplified by the same examples as those given above for the substituent on the aryl group in the arylalkyl group for $R^1$, which may be substituted for.

With respect to X above, B for a protecting group of by hydroxyl group in formula: $—CHO$ or $—CH_2OB$ is exemplified those protecting groups of hydroxyl group in the hydroxyl group as a substituent of lower alkyl group of $R^1$ mentioned above, preferably alkanoyl group of 2 to 10 carbon atoms.

Regarding the protecting group of amino group represented by M, mention is made those of amino-protecting groups disclosed herein before.

In the present invention, the salt of the compound of general formula (I) is preferably a physiologically acceptable salt, exemplified by salts with inorganic bases, salts with organic bases, salts with inorganic acids, salts with organic acids and salts with basic or acidic amino acids. Preferable salts with inorganic bases include alkali metal salts such as sodium salt and potassium salt, alkaline earth metal salts such as calcium salt and magnesium salt, aluminum salt and ammonium salt. Preferable salts with organic bases include salts with trimethylamine, triethylamine, pyridine, picoline, ethanolamine, diethanolamine, triethanolamine, dicyclohexylamine and N,N'-dibenzylethylenediamine etc. Preferable salts with inorganic acids include salts with hydrochloric acid, hydrobromic acid, nitric acid, sulfuric acid and phosphoric acid. Preferable salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid etc. Preferable salts with basic amino acids include salts with arginine, lysine and ornithine. Preferable salts with acidic amino acids include salts with aspartic acid and glutamic acid.

With respect to compound (I), $R^1$ is preferably $C_{1-6}$ alkyl which may be substituted by indolyl or aryl, especially indol-3-ylmethyl, benzylmethyl, methyl, isopropyl, l-naphthyl or the like, $R^2$ is preferably branched $C_{3-6}$ alkyl, phenyl-$C_{1-6}$ alkyl or hydrogen atom, especially sec-butyl, benzyl, hydrogen atom or the like, $R^3$ is preferably branched $C_{3-6}$ alkyl, especially sec-butyl, hydrogen atom, $R^4$ is preferably those being lower ($C_{1-6}$) alkyl which may be substituted by aryl or alicyclic hydrocarbon-alkyl or aryl which may be substituted as respective $R^5$, $R^6$, $R^7$, $R^8$ and $R^9$, and is more preferably a $C_{2-6}$ alkanoyl, sulfonyl, carbonyloxy, carbamoyl or thiocarbamoyl group which is substituted by $C_{1-6}$ alkyl, aryl, arylalkyl or cycloalkyl, especially an alkanoyl group substituted by $C_{9-12}$ aryl or a sulfonyl, carbamoyl or thiocarbamoyl group substituted by aryl of more than 9 carbon atoms or $C_{1-6}$ alkyl. $R^{4'}$is preferably those being lower ($C_{1-6}$) alkyl which may be substituted by aryl or alicyclic hydrocarbon-alkyl or aryl which may be substituted as respective $R_5$, $R_6$ and $R_7$, and is more preferably a $C_{2-6}$ alkanoyl, sulfonyl or carbonyloxy group which is substituted by $C_{1-6}$ alkyl, aryl, arylalkyl or cycloalkyl, especially an alkanoyl group substituted by $C_{9-12}$ aryl or a sulfonyl group substituted by aryl of more than 9 carbon atoms or $C_{1-6}$ alkyl. X is preferably $—CHO$ or $—CH_2OH$, m is preferably 0 or 1 and n is preferably 0.

Particularly preferable compounds of general formula (I) include N-(4-toluenesulfonyl)-(L)-isoleucyl-(L)-tryptophanal, N-(t-butoxycarbonyl)-(L)-isoleucyl-(L)-tryptophanal, N-(1-naphthylsulfonyl)-(L)-isoleucyl-(L)-tryptophanal, N-(benzyloxycarhonyl)-(L)-isoleucyl-(L)-isoleucyl-(L)-tryptophanal, N-(1-naphthylsulfonyl)-(L)-isoleucyl-(L)-isoleucyl-(L)-tryptophanal, N-benzylcarbamoyl-(L)-isoleucyl-(L)-tryptophanal, N-[(2-cyclohexylethyl)carbamoyl]-(L)-isoleucyl-(L)-tryptophanal, N-(3-trifluoromethylphenylcarbamoyl)-(L)-isoleucyl-(L)-tryptophanal, N-(2propylpentanoyl)-(L)-tryptophanal, N-dibenzylacetyl-(L)-tryptophanal, N-dibenzylacetyl-(L)-phenylalanal, N-benzyloxycarbonyl- (L)-isoleucyl-(L)phenylalanal, N-(1-naphthylsulfonyl)-(L)-isoleucyl-(L)-phenylalaninal, N-(1-naphthylsulfonyl)-(L)-isoleucylalanal, N-benzyloxycarbonyl-(L)-leucyl-(L)-leucylglycinal, N-(2-propylpentanoyl)-(L)-alanyl-(L)-tryptophanal, N-(2-propylpentanoyl)-(L)-valyl-(L)-tryptophanal, N-(1-naphthylsulfonyl)-(L)-isoleucyl-(L)-tryptophanol, N-dibenzylacetyl-(L)-tryptophanol and N-(1naphthylsulfonyl)-(L)-isoleucyl-(L)-alaninol.

Production methods for compound (I) are hereinafter described in detail.

Method A

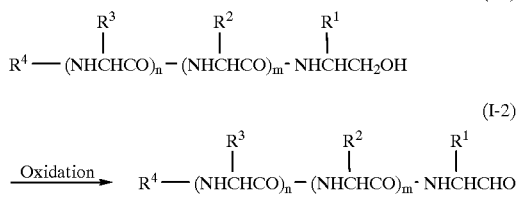

In the above formulas, the symbols have the same definitions as those shown above.

This oxidation is carried ouut by a known oxidizing reaction. Such reactions include chromic acid oxidations such as Jones' oxidation, using chromium oxide-sulfuric acid-pyridine, Collins oxidation, using chromiumpyridine complex, oxidation with pyridinium chlorochromate (PCC) and oxidation with pyridinium dichromate (PDC), oxidation with activated DMSO and oxidation with oxoammonium salt.

In the case of an optically active configuration, this oxidation is advantageously carried out by activated dimethyl sulfoxide (DMSO) oxidation. Activated DMSO oxidation is carried out in a solvent in the presence of both DMSO and an electrophilic reagent. This solvent is exemplified by ethers such as ethyl ether, isopropyl ether, tetrahydrofuran and dioxane, aromatic hydrocarbons such as benzene, toluene and xylene, N,N-dimethylformamide (DMF), halogenated hydrocarbons such as chloroform and dichloromethane, pyridine and dimethyl sulfoxide, chosen as appropriate according to the kind of electrophilic reagent. Methods of activated DMSO oxidation include the dicyclohexylcarbodiimide (DCC) method, the acetic anhydride method, the phosphorus pentoxide method, the chlorine method, the sulfur trioxide-pyridine method, the ketene-imineenamine method and the mercury (II) acetate method, named according to the electrophilic reagent used. This oxidation is advantageously carried out by the sulfur trioxide-pyridine method, in which oxidation is achieved using a sulfur trioxide-pyridine complex as a DMSO activator reagent in the presence of triethylamine. This reaction can also be carried out with dimethyl sulfoxide as a solvent. The amount of triethylamine and sulfur trioxidepyridine complex used is 1 to 10 mol, preferably 2 to 5 mol per mol of compound (I-1). Reaction temperature is −70 to 80° C., preferably −20 to 40° C., reaction time being 0.5 to 10 hours.

Aldehyde derivative (I-2) thus obtained may be isolated and purified by known means of separation and purification such as concentration, concentration under reduced pressure, solvent extraction, crystallization, recrystallization, redissolution and chromatography.

Starting material compound of the Method A can, for example, be produced as follows:

Method B

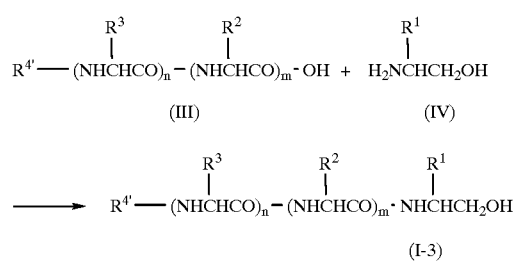

In the above formulas, the symbols have the same definitions as those shown above.

In this method, compound (III) or its reactive derivative (or salt thereof) is reacted with compound (IV) or its derivative reactive at the amino group thereof (or salt thereof) to yield compound (I-3). Preferable derivatives of compound (IV) reactive at the amino group thereof include Schiff's base type imino or enamine form tautomeric isomers resulting from reaction of compound (IV) and a carbonyl compound such as aldehyde or ketone, silyl derivatives resulting from reaction of compound (IV) and a silyl compound such as bis(trimethylsilyl)acetamide, mono(trimethylsilyl)acetamide or bis(trimethylsilyl)urea, and derivatives resulting from reaction of compound (IV) and phosphorus trichloride or phosgene. Preferable salts of compound (IV) and its reactive derivatives are exemplified by the same acid adduct salts as specified for compound (I) above.

Preferable derivatives of compound (III) reactive at the carboxyl group thereof include acid halides, acid anhydrides, activated amides and activated esters. Other preferable reactive derivatives include acid chlorides, acid azides, mixed acid anhydrides such as those with a substituted phosphoric acid such as dialkylphosphoric acid, phenylphosphoric acid, diphenylphosphoric acid, dibenzylphosphoric acid or halogenated phosphoric acid, or with dialkylphosphorous acid, sulfurous acid, thiosulfuric acid or sulfuric acid, or with a sulfonic acid such as methanesulfonic acid, or with an aliphatic carboxylic acid, such as acetic acid, propionic acid, butyric acid, isobutyropivalic acid, pentanoic acid, isopentanoic acid or trichloroacetic acid, or with an aromatic carboxylic acid such as benzoic acid, symmetric acid anhydrides, activated amides with imidazole, 4-substitutional imidazole, dimethylpyrazole, triazole or tetrazole, activated esters such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenylthio ester, p-nitrophenyl ester, p-cresylthio ester, carboxymethylthio ester, pyranyl ester, pyridyl ester, piperidyl ester and 8-quinolylthio ester, and esters with N-hydroxy compounds such as N,N-dimethylhydroxylamine, 1-hydroxy-2-(1H)-pyridone, N-hydroxysuccinimide, N-hydroxyphthalmide and 1-hydroxy-1H-benzotriazole. These reactive derivatives can be optionally chosen according to kind of compound (III) used. Preferable salts of reactive derivatives of compound (III) include salts with bases, exemplified by alkali metal salts such as sodium salt and potassium salt, alkaline earth metal salts such as calcium salt and magnesium salt, ammonium salt, and organic base salts such as trimethylamine salt, triethylamine salt, pyridine salt, picoline salt, dicyclohexylamine salt and N,N-dibenzylethylenediamine salt. This reaction is normally carried out in an ordinary solvent such as water, an alcohol such as methanol or ethanol, acetone, dioxane, acetonitrile, chloroform, methylene chloride, ethylene chloride, tetrahydrofuran, ethyl acetate, N,N-dimethylformamide or pyridine, but can be carried out in any other organic solvent, as long as it does not interfere with the reaction. These ordinary solvents may be used in mixture with water.

When compound (III) is used in the form of free acid or salt thereof, this reaction is preferably carried out in the presence of an ordinary condensing agent such as N,N'-dicyclohexylcarbodiimide, N-cyclohexyl-N'-morpholinoethylcarbodiimide, N-cyclohexyl-N'-(4diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonylbis(2-methylimidazole), pentamethyleneketene-N-cyclohexylimine, diphenylketene-N-cyclohexylimine, ethoxyacetylene, 1-alkoxy-1-chloroethylene, trialkyl phosphite, ethyl polyphosphate, isopropyl polyphosphate, phosphorus oxychloride, diphenylphosphorylazide, thionyl chloride, oxalyl chloride, a lower alkyl haloformate such as ethyl chloroformate or isopropyl chloroformate, triphenylphosphine, 2-ethyl-7-hydroxybenzisoxazolium salt, 2-ethyl-5-(m-sulfophenyl)isoxazolium hydroxide intramolecular salt, N-hydroxybenzotriazole, 1-(p-chlorobenzenesulfonyloxy)-6-chloro-1H-benzotriazole, or what is called Wilsmeier's reagent as prepared by reaction of N,N-dimethylformamide and thionyl chloride, phosgene, trichloromethyl chloroformate or phosphorus oxychloride. This reaction may also be carried out in the presence of an inorganic or organic base such as alkali metal hydrogen carbonate tri(lower)alkylamine, pyridine, N-(lower)-alkylmorpholine or N,N-di(lower)alkylbenzylamine. Although reaction temperature is not subject to limitation, this reaction is normally carried out under cooling to heating conditions.

Compounds (I-1) and (I-3) are converted to compound (I-4).

Method C

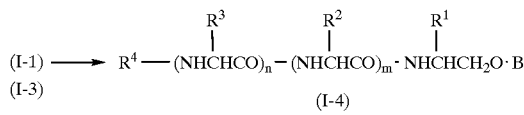

In the above formula, B is a protective group for hydroxyl group and the other symbols have the same definition as those shown above.

The reaction is conducted by reacting B-OH or its reactive derivative or its salt with compound (I-1) or its salt. This reaction is conducted as the same manner as the reaction of compound (III) or its reactive derivative of carboxyl group with compound (IV).

Method D

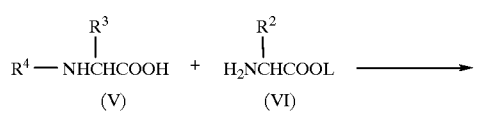

-continued

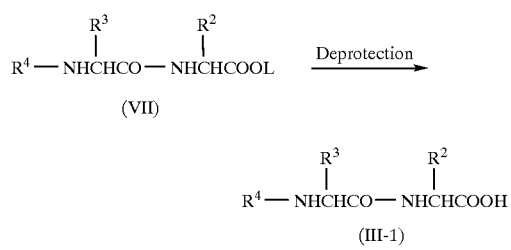

In the above formulas, L represents a carboxy-protecting group; the other symbols have the same definitions as above.

The carboxy-protecting group for L is exemplified by protecting groups in common use in the field of peptide synthesis, such as ester derivatives.

In this method, compound (V) or its derivative reactive at the carboxyl group thereof (or salt thereof) is reacted with compound (VI) or its derivative reactive at the amino group thereof (or salt thereof) to yield compound (VII), which is then subjected to a deprotecting reaction to remove the carboxy-protecting group to yield compound (III-1). The reaction of compound (V) or its derivative reactive at the carboxyl group thereof (or salt thereof) and compound (VI) or its derivative reactive at the amino group thereof (or salt thereof) is carried out in the same manner as method B.

The deprotecting reaction of compound (VII) to remove its carboxy-protecting group can be achieved by any common method of carboxy protective group-removing reaction, such as deprotection by hydrolysis, reduction or Lewis acid. When the carboxy-protecting group is an ester, it can be removed by hydrolysis or deprotection using Lewis acid, preferably hydrolysis in the presence of a base or acid. Preferable bases include inorganic bases such as alkali metal hydroxides (e.g., sodium hydroxide, potassium hydroxide), alkaline earth metal hydroxides (e.g., magnesium hydroxide, calciurm hydroxide), alkali metal carbonates (e.g., sodium carbonate, potassium carbonate), alkaline earth metal carbonates (e.g., magnesium carbonate, calcium carbonate), alkali metal bicarbonates (e.g., sodium bicarbonate, potassium bicarbonate), alkali metal acetates (e.g., sodium acetate, potassium acetate), alkaline earth metal phosphates (e.g., magnesium phosphate, calcium phosphate), alkali metal hydrogen phosphates (e.g., disodium hydrogen phosphate, dipotassium hydrogen phosphate), and organic bases such as trialkylamines (e.g., trimethylamine, triethylamine), picoline, N-methylpyrrolidine, N-methylmorpholine, 1,5-diazabicyclo[4,3,0]non-5-ene, 1,4-diazabicyclo[2,2,2]non-5-ene and 1,8-diazabicyclo[5,4,0]-7-undecene. Hydrolysis using a base is often carried out in water or a hydrophilic organic solvent or mixture thereof. Preferable acids include organic acids (e.g., formic acid, hydrobromic acid, sulfuric acid).

This hydrolysis is normally carried out in an organic solvent, water or a mixture thereof. Reaction temperature, not subject to limitation, is chosen as appropriate according to kind of carboxy-protecting group and method of deprotection. Deprotection using a Lewis acid is achieved by reacting compound (VII) (or salt thereof) with a Lewis acid such as a boron trihalide (e.g., boron trichloride, boron trifluoride), a titanium tetrahalide (e.g., titanium tetrachloride, titanium tetrabromide), an aluminum trihalide (e.g., aluminum chloride, aluminum bromide) or a trihaloacetic acid (e.g., trichloroacetic acid, trifluoroacetic acid). This deprotecting reaction is preferably carried out in the presence of a cation capturing agent (e.g., anisole, phenol)

and normally carried out in a solvent which does not interfere with the reaction, such as a nitroalkane (e.g., nitromethane, nitroethane), an alkylene halide (e.g., methylene chloride, ethylene chloride), diethyl ether or carbon disulfide. These solvents may be used in mixture.

Deprotection by reduction is preferably applied to removing the protecting groups such as esters of haloalkyls (e.g., 2-iodoethyl, 2,2,2-trichloroethyl) and esters of aralkyls (e.g., benzyl). Methods of reduction for this deprotecting reaction include reduction with a combination of a metal (e.g., zinc, zinc amalgam) or a chromium compound salt (e.g., chromium (II) chloride, chromium (II) acetate) and an organic or inorganic acid (e.g., acetic acid, propionic acid, hydrochloric acid), and ordinary catalytic reduction in the presence of an ordinary metal catalyst (e.g., palladium-carbon, Raney nickel). Although reaction temperature is not subject to limitation, this reaction is normally carried out under cooling, room temperature or heating conditions.

Method E

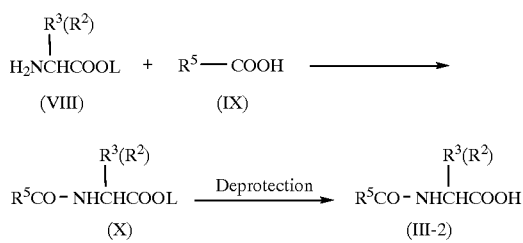

In the above formulas, the symbols have the same definitions as those shown above.

In this method, compound (IX) or its activated derivative at the carboxyl group thereof (or salt thereof) is reacted with compound (VIII) or its activated derivative at the amino group thereof (or salt thereof) to yield compound (X), which is then subjected to a deprotecting reaction to remove its carboxy-protecting group to yield compound (III-2). This method is carried out in the same manner as method D.

Method F

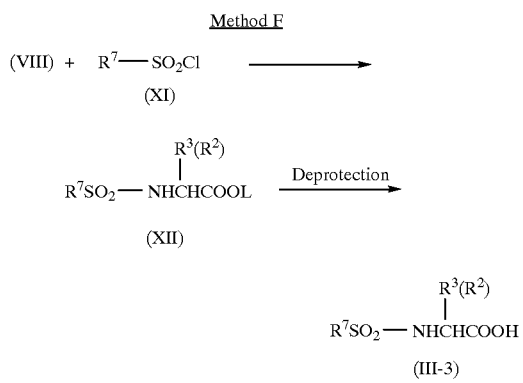

In the above formulas, the symbols have the same definitions as those shown above.

In this method, compound (XI) (or salt thereof) is reacted with compound (VIII) (or salt thereof) to yield compound (XII), which is then subjected to a deprotecting reaction to remove its carboxy-protecting group to yield compound (III-3). The reaction of compounds (VIII) with (XI) is carried out in an appropriate solvent. This solvent is exemplified by aromatic hydrocarbons such as benzene, toluene and xylene, ethers such as dioxane, tetrahydrofuran and dimethoxyethane, alcohols such as methanol, ethanol and propanol, ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone and mixtures thereof.

The reaction of compounds (VIII) with (XI) is carried out in the presence of an appropriate base exemplified by alkali metal salts such as sodium hydroxide, potassium hydroxide, potassium carbonate, sodium carbonate and sodium hydrogen carbonate, amines such as pyridine, triethylamine and N,N-dimethylaniline, sodium hydride and potassium hydride. The amount of these bases used is preferably about 1 to 5 mol per mol of compound (VII). The reaction is carried out at temperatures of normally from –20 to 150° C., preferably from about –10 to 100° C. Compound (XII) thus obtained is subjected to a deprotecting reaction to yield compound (III-3). This deprotection is carried out in the same manner as the deprotecting reaction in method D.

Method G

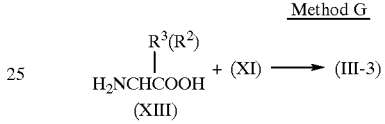

In the above formulas, the symbols have the same definitions as those shown above.

In this method, compound (XII) (or salt thereof) is reacted with compound (XI) (or salt thereof) to yield compound (III-2). This sulfonylation is normally carried out under what is called Schotten Baumann's conditions, in which amino acid derivative (XIII), prepared as a sodium salt in an aqueous solution, is reacted with compound (XI) and then acidified.

Method H

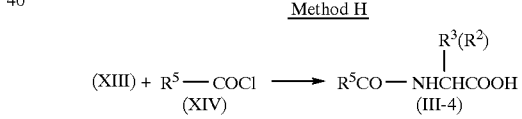

In the above formulas, the symbols have the same definitions as those shown above.

In this method, compound (XEII) (or salt thereof) is reacted with compound (XI) (or salt thereof) to yield compound (III-4). This acylation is carried out in the same manner as method G.

Method I

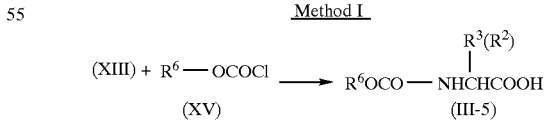

In the above formulas, the symbols have the same definitions as those shown above.

In this method, compound (XIII) (or salt thereof) is reacted with compound (XV) (or salt thereof) to yield compound (III-5). This method is carried out in the same manner as method H.

Method J

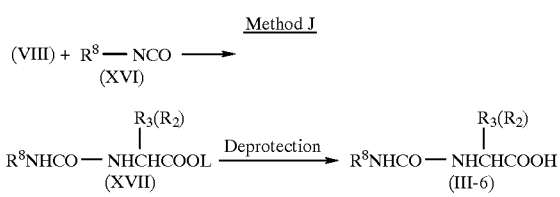

In the above formulas, the symbols have the same definitions as those shown above.

In this method, compound (VIII) (or salt thereof) is reacted with compound (XVI) to yield compound (XVII), which is then subjected to a deprotecting reaction to remove its carboxy-protecting group to yield compound (III-5). The reaction of compound (VIII) (or salt thereof) and compound (XVI) is carried out in an appropriate solvent. This solvent is exemplified by aromatic hydrocarbons such as benzene, toluene and xylene, ethers such as dioxane, tetrahydrofuran and dimethoxyethane, ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone and mixtures thereof. The amount of compound (XVI) used is preferably about 1 to 5 mol per mol of compound (VIII). The reaction is normally carried out at temperatures of −20 to 150° C., preferably about −10 to 100° C. Compound (XVII) thus obtained is subjected to a deprotecting reaction to yield compound (III-6). This deprotection is carried out in the same manner as the deprotection in method D.

Method K

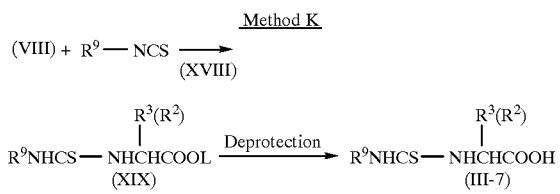

In the above formulas, the symbols have the same definitions as those shown above.

In this method, compound (VIII) (or salt thereof) is reacted with compound (XVIII) to yield compound (XIX), which is then subjected to a deprotecting reaction to remove its carboxy-protecting group to yield compound (III-7). This reaction is carried out in the same manner as method J.

Starting material compound (I-1) for methods A and C can also be produced as follows:

Method L

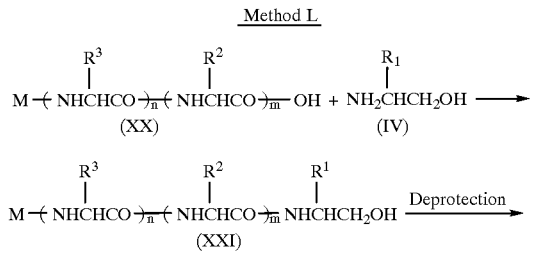

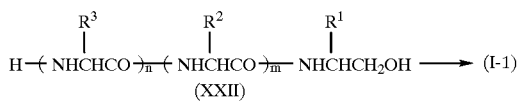

In the above formulas, M represents an amino-protecting group; the other symbols have the same definitions as those shown above.

The amino-protecting group for M is exemplified by protecting groups in common use in the field of peptide synthesis, such as oxycarbonyl derivatives, with preference given to benzyloxycarbonyl.

In this method, compound (XX) or its derivative reactive at the carboxyl group thereof (or salt thereof) is reacted with compound (IV) or its derivative reactive at the amino group thereof (or salt thereof) to yield compound (XXI), which is then subjected to a deprotecting reaction to remove its amino-protecting group to yield compound (XXII). The reaction of compound (XX) or its derivative reactive at the carboxyl group thereof (or salt thereof) with compound (IV) or its derivative reactive at the amino group thereof (or salt thereof) is carried out in the same manner as method B. In the amino-protecting group removing reaction of compound (XXI), the amino-protecting group can be removed by any commonly used method of reaction to remove the amino-protecting group. For example, the benzyloxycarbonyl group is removed by catalytic reduction in the presence of a commonly used metal catalyst (e.g., palladium-carbon, Raney nickel). Reaction temperature is not subject to limitation; the reaction is normally carried out under cooling, room temperature or heating conditions. Then, compound (XXII) is acylated in the same manner as the reaction of compounds (VIII) and (IX) in method E or the reaction of compounds (XIII) and (XIV) in method H, sulfonylated in the same manner as the reaction of compounds (VIII) and (XI) in method F, then oxycarbonylated in the same manner as the reaction of compounds (XIII) and (XV) in method I, carbamoylated in the same manner as the reaction of compounds (VIII) and (XVI) in method J, and then thiocarbamoylated in the same manner as the reaction of compounds (VIII) and (XVIII) in method K, to yield compound (I-1).

In the present invention, the compound of formula (I) can be administered orally or parenterally, as formulated by admixing an effective dose with a physiologically acceptable carrier, excipient or diluent in the form of solid preparations such as tablets, capsules, granules and powders, or liquid preparations such as syrups and injectable preparations.

Pharmaceutically acceptable carriers are various organic or inorganic carrier substances in common use as pharmaceutical materials, including excipients, lubricants, binders and disintegrating agents for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary. Preferable excipients include lactose, sucrose, D-mannitol, starch, crystalline cellulose and light silicic anhydride. Preferable lubricants include magnesium stearate, calcium stearate, talc and colloidal silica. Preferable binders include crystalline cellulose, sucrose, D-mannitol, dextrin, hydroxypropyl cellulose, hydroxypropylmethyl cellulose and polyvinylpyrrolidone. Preferable disintegrating agents include starch, carboxymethyl cellulose, carboxymethyl cellulose calcium, crosscalmellose sodium and carboxymethyl starch sodium. Preferable solvents include water for injection, alcohol, propylene glycol, macrogol, sesame oil and corn oil. Preferable dissolution aids include polyethylene glycol, propylene glycol, D-mannitol, benzyl benzoate, ethanol, tris-aminomethane, cholesterol, triethanolamine, sodium carbonate and sodium citrate. Preferable suspending agents include surfactants such as stearyltriethanolamine, sodium lauryl sulfate, laurylaminopropionic acid, lecithin, benzalkonium chloride, benzethonium chloride and monostearic glycerol, and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose. Preferable isotonizing agents include sodium chloride, glycerol and D-mannitol. Preferable buffers include buffer solutions of phosphates, acetates, carbonates and citrates. Preferable soothing agents include benzyl alcohol. Preferable preservatives include p-oxybenzoic acid esters, chlorobutanol, benzyl alcohol, phenethyl alcohol, dehydroacetic acid and sorbic acid. Preferable antioxidants include sulfites and ascorbic acid.

The compound of formula (I) potently inhibits cathepsin L, excellently suppresses bone resorption and is of low toxicity. The compound of general formula (I) can therefore be used to prevent or treat osteoporosis in mammals (e.g., mice, rats, rabbits, dogs, cats, bovines, swines, humans).

When using as a prophylactic/therapeutic agent, compound (I) (or salt thereof) is administered at 1 to 500 mg, preferably 10 to 200 mg daily for each adult in the case of oral administration.

The compound of formula (I) can also be used in a simple in vitro assay for screening and selecting compounds that affect bone resorption. The screening method involves adding a compound of formula (I) to an in vitro assay suitable for measuring bone resorption, such as the method of Raisz [*Journal of Clinical Investigation*, 44, 103–116 (1965)]. The inhibition of bone resorption by the compound of formula (I) is recorded. (Experimental Example 9 below, sets out the details of such an assay.) The test compound is then added to the assay and bone resorption is again measured. Test compounds can include, for example, proteins, chemicals or drugs. Any changes in the bone resorption inhibitory activity of the compound of formula (I) would indicate that the test compound has an influence on bone resorption. Such compounds may then be further evaluated.

The action of compound (I) is hereinafter described by means of the following experimental examples.

Experimental Example 1: Cloning of cathepsin L cDNA of human renal origin

To amplify human cathepsin L cDNA by the PCR method, four primers were synthesized in accordance with a reported base sequence of cathepsin L of human renal origin [S. Gal and M. M. Gottesman, Biochem. J., 253 303 (1988)] as follows:

Sense primer No. 1:
  5'-TTTTCAGGGGGCAGTAAGAT-3' (SEQ ID NO: 1)
Sense primer No. 2:
  5'-pCCGGATCCGGCTTTTTAGGATTGGTCTA-3' (SEQ ID NO: 2)
Antisense primer No. 3:
  5'-GGGGGCTGGTAGACTGAAGA-3' (SEQ ID NO: 3)
Antisense primer No. 4:
  5'-pCCGGATCCATTCCTCCCATGCATGCGOC-3' (SEQ ID NO: 4)

3 µl of a solution of the human renal cDNA library λgt11 (CLONTECH Laboratories, Inc.) and 50 µl of distilled water were mixed. After incubation at 95° C. for 5 minutes, the mixture was immediately cooled in ice. Two primers (Nos. 1 and 3 above, 50 pmol of each) were added, and PCR was carried out as directed in the instruction manual for the kit supplied from Cetus/Perkin-Elmer, in which a series of reactions at 94° C. for 1 minute, 55° C. for 2 minutes and 72° C. for 3 minutes was repeated in 50 cycles. To the reaction mixture were added two other primers (Nos. 2 and 4 above, 50 pmol of each), and PCR was carried out in the same manner as above. The PCR product was separated by electrophoresis on 1.2% agarose gel; an amplified DNA fragment was seen at a position corresponding to the size (1132 bp) expected from the base sequence of cathepsin L of human renal origin. This DNA fragment was recovered from the gel and subcloned to the plasmid vector pBluescript$^R$ II SK+(produced by STRATAGENE). The base sequence of the cDNA portion, determined by the dideoxynucleotide synthetic chain termination method [J. Messing et al., Nucleic Acids Res., 9, 309 (1981)], proved identical with the reported sequence. The plasmid containing this cDNA fragment was named pHCL-5.

Experimental Example 2: Expression of human cathepsin L in *Escherichia coli* MM294(DE3)

The cDNA of Experimental Example 1 was cleaved with restriction enzyme EcoRI and a 798 bp fragment (which encodes a part of the human cathepsin L precursor and the whole matured human cathepsin L) was recovered. To both ends of this fragment was ligated a BamHI linker (5'-pCCCGGATCCGGG-3'; sequence ID No. 5); the ligation product was inserted to the plasmid vector pET-3c for expression in *Escherichia coli* [Methods in Enzymology, ed. D.V. Goeddel, 185 68, Academic Press (1990)]. The thus-constructed plasmid was designated pET-HCLα. *Escherichia coli* MM294(DE3) was transformed with pET-HCLα to express human cathepsin L in the presence of the T7 promoter [Methods in Enzymology, 185, 60 (1990)]. The thus-obtained *Escherichia coli* transformant [*Escherichia coli* JM109/pTBN-HCLneo, harboring the plasmid pTBN-HCLneo, has been deposited under accession number IFO 15341 at the Institute for Fermentation, Osaka, since Jun. 12, 1992, and under accession number FERM BP 3897 at the Fermentation Research Institute, Agency of Industrial Science and Technology since Jun. 22, 1992.] was cultured; cells were disrupted by sonication and subjected to SDS-PAGE; a unique band appeared near 30 kDal, corresponding to human cathepsin L. Since the expressed product formed an inclusion body, human cathepsin L was partially purified from the precipitated fraction of the ultrasonically disrupted transformant.

Experimental Example 3: Preparation of antiserum to recombinant human cathepsin L The partially purified recombinant human cathepsin L described in Reference Example 2 was mixed with an equal volume of Freund's complete adjuvant and about 1 ml was inoculated to a rabbit. Later, a mixture of a partially purified human cathepsin L and an equal volume of Freund's incomplete adjuvant was injected thrice at 10-day intervals, and blood was collected seven days after final injection. The obtained blood was kept standing at 37° C. for 30 minutes and then at 4° C. overnight, after which it was centrifuged to yield a human cathepsin L antiserum.

Experimental Example 4: Preparation of recombinant DNA for expression of human cathepsin L gene in animal cells After the plasmid pHCL-5 (described in Experimental Example 1) was digested with restriction enzyme BanmHI, a fragment of human cathepsin L cDNA was recovered by agarose gel electrophoresis. Next, this cDNA fragment was inserted to the restriction enzyme BglII site of the vector pTB551 for transient expression in animal cells [prepared by converting the EcoRI site to BglII site in the plasmid pTB389 described by Ono et al. in Science, 236, 1116 (1989)] by the action of T4 DNA ligase and ATP, to yield the expression plasmid pTB-HCL. MuLV-LTR was inserted between the restriction enzyme HindIII and ClaI sites of pTB-H(CL to yield the expression plasmid pTBN-HCL (FIG. 1).

Experimental Example 5: Preparation of recombinant DNA for expression of human cathepsin L gene in animal cells To obtain an animal cell line that stably expresses human cathepsin L, the drug resistance marker neo gene was inserted to the vector pTBN-HCL described in Experimental Example 4 as follows: Namely, a fragment comprising the SV40 early promoter and the neo gene was inserted between the restriction enzyme ClaI and SalI sites of the plasmid PTBN-HCL to yield the plasmid pTBN-HCLneo (FIG. 1).

Experimental Example 6: Expression of human cathepsin L gene in animal cells

Using the plasmid described in Experimental Example 5 (pTBN-HCLneo), mouse myeloma Sp2/0 cells were transformed as follows: Sp2/0 cells, cultivated in an ASF104 medium supplemented with 5% FCS (5% FCS/ASF medium), were suspended in PBS(−) [the same as Dullbecco's PBS but $CaCl_2$ and $MgCl_2$ are removed] to adjust $1 \times 10^7$ cells/ml. 500 $\mu$l of this suspension was injected to a cuvette, 10 $\mu$g of said plasmid DNA was added, and the mixture was kept standing on ice for 5 minutes. This liquid was pulsated at 125 $\mu$F and 300 V, using a gene pulsar (produced by Bio-Rad Laboratories), and then again kept standing on ice for 10 minutes. This liquid was transferred to 10 ml of 5% FCS/ASF104 medium and cultured at 37° C. in the presence of 5% carbon dioxide. Forty-eight hours later the culture was transferred to a selection medium (5% FCS/ASF104 medium containing 200 fg/ml G418) and cultured on a 24-well plate for 2 weeks. A number of colonies emerged, each of which was transferred to an ASF104 medium containing 200 $\mu$g/ml G418 and cultured, followed by Western blot analysis of the culture supernatant using the human cathepsin L antiserum prepared in Experimental Example 3. In response to the antiserum, unique bands appeared having molecular weights of about 40,000 to 30,000 and lower molecular weights; they were identified as a precursor of human cathepsin L and processing products thereof, as estimated from their molecular weights. The culture supernatant was assayed for cathepsin L enzyme activity, in accordance with the method of A. J. Barrett and H. Kirschke [Methods in Enzymology, 80, 535 (1981)]; human cathepsin L activity was detected.

These findings confirm that transformed mouse myeloma cells expressing cathepsin L were obtained; these were designated as mouse myeloma Sp-HCL26.

Experimental Example 7: Purification of human cathepsin L

The strain obtained in Experimental Example 6, showing high expression of cathepsin L, (mouse myeloma Sp-HCL26, transformed with the plasmid pTBN-HCLneo, has been deposited under accession number IFO 50371 at the Institute for Fermentation, Osaka (IFO) since Jun. 16, 1992 and under accession number FERM BP 3902 at the Fermentation Research Institute (FRI), Agency of Industrial Science and Technology since Jun. 24, 1992), was cultured in 20 ml of an ASF104 medium supplemented with 10% FCS and 200 $\mu$g/ml G418, after which it was transferred to 50 ml of a serumfree selection medium (ASF104 medium supplemented with 200 $\mu$g/ml G418) and cultured for 5 days. After the culture supernatant was applied to a column of CM-Sephadex C-50 (25×4.4 cm), the column was washed with buffer A (20 mM sodium acetate, 1 mM EDTA, pH 5.5), followed by elution on a sodium chloride (NaCl) density gradient from 0 to 1M, to elute human cathepsin L near an NaCl concentration of about 0.4M. This fraction was applied to a Mono S column (HR5/5) of an FPLC system (produced by Pharmacia), followed by column washing and human cathepsin L elution in the same manner as above. The human cathepsin L fraction, eluted near an NaCl concentration of about 0.36M, was concentrated to yield a purified preparation.

Experimental Example 8: Determination of human cathepsin L inhibitory activity

The recombinant human cathepsin L purified in Experimental Example 7 was diluted with a diluent [0.1% Brij 35 (produced by Sigma Chemical Company)] to a concentration of 1 $\mu$g/ml. To 1 $\mu$l of this enzyme dilution, 46 $\mu$l of the diluent, 2 $\mu$l of 0.1M DTT and 25 $\mu$l of an activator/buffer (340 mM sodium acetate, 60 mM acetic acid, 4 mM disodium EDTA, pH 5.5) were added. To this mixture were added a 1 $\mu$l sample, diluted to $10^{-2}$M with dimethyl sulfoxide (DMSO), and 25 $\mu$l of 20 $\mu$M Z-Phe-Arg-NMec (enzyme substrate solution), followed by incubation at 30° C. for 10 minutes, after which 100 $\mu$l of a reaction stopper (100 mM sodium monochloroacetate, 30 mM sodium acetate, 70 mM acetic acid, pH 4.3) was added. This reaction was carried out on a 96-well fluoroplate (produced by Labo Systems).

After the reaction was stopped, the fluorescence intensity of free aminomethylcoumarin was determined at a wavelength of 450 nm (excitation wavelength=365 nm), using a fluorometer FCA (produced by Baxter). For a control, 1 $\mu$l of sample-free DMSO was added instead; the fluorometric value obtained from this control reaction was taken as 100% activity. When the residual activity was not higher than 10%, the sample solution was further diluted and then assayed for residual activity in the same procedure as above to obtain the $IC_{50}$ value. The results are given in Table 1.

TABLE 1

| Compound (Example No.) | Cathepsin L Inhibitory Activity [$IC_{50}$ Value (M)] |
| --- | --- |
| 101 | $2.2 \times 10^{-9}$ |
| 102 | $3.3 \times 10^{-9}$ |
| 103 | $1.9 \times 10^{-9}$ |
| 107 | $1.1 \times 10^{-8}$ |
| 108 | $5.4 \times 10^{-9}$ |
| 109 | $1.0 \times 10^{-8}$ |
| 110 | $1.6 \times 10^{-8}$ |
| 111 | $1.4 \times 10^{-8}$ |
| 112 | $3.8 \times 10^{-7}$ |
| 114 | $6.1 \times 10^{-9}$ |
| 115 | $4.8 \times 10^{-8}$ |
| 117 | $2.0 \times 10^{-9}$ |
| 118 | $2.2 \times 10^{-7}$ |
| 122 | $3.2 \times 10^{-8}$ |
| 124 | $5.3 \times 10^{-9}$ |
| 128 | $1.9 \times 10^{-8}$ |
| 129 | $8.5 \times 10^{-8}$ |
| 132 | $9.9 \times 10^{-10}$ |
| 135 | $1.0 \times 10^{-9}$ |
| 143 | $1.7 \times 10^{-9}$ |
| 144 | $2.4 \times 10^{-9}$ |
| 150 | $6.1 \times 10^{-9}$ |
| 153 | $3.1 \times 10^{-9}$ |
| 154 | $9.5 \times 10^{-10}$ |
| 158 | $1.4 \times 10^{-9}$ |
| 167 | $4.3 \times 10^{-8}$ |
| 168 | $2.6 \times 10^{-8}$ |
| 175 | $1.9 \times 10^{-8}$ |
| 188 | $3.7 \times 10^{-8}$ |
| 190 | $5.5 \times 10^{-8}$ |
| 191 | $4.7 \times 10^{-9}$ |
| 192 | $4.2 \times 10^{-9}$ |
| 193 | $3.9 \times 10^{-9}$ |

Experimental Example 9: Bone resorption suppressing action

Bone resorption was measured by the method of Raisz [Journal of Clinical Investigation, 44, 103–116 (1965)].

Specifically, one Sprague-Dawley rat, at 18 days of gestation, was given 50 μCi of $^{45}$Ca (calcium isotope, in CaCl$_2$ solution) by subcutaneous injection. On the following day, the animal was laparotomized and fetal rats aseptically removed. Both forearm bones (radius and ulna) were cut out from the body of each fetus under an anatomical microscope, and connective tissue and cartilages were removed to the maximum possible extent, to prepare bone culture samples. Each bone fragment was pre-cultured at 37° C. for 24 hours in 0.6 ml of BGJb medium (Fitton-Jackson modification, GIBCO Laboratories, United States) prepared by adding bovine serum albumin (final concentration 2 mg/ml), after which it was transferred to the same medium as above but containing each compound (final concentration 10 μg/ml or 10 μM) and cultured for two more days. $^{45}$Ca radioactivity in the medium and $^{45}$Ca radioactivity in the bone were then measured, and the percent ratio of $^{45}$Ca released from the bone to the medium was calculated using the following equation:

$$\text{Percent ratio of } ^{45}\text{Ca released from bone to medium} = \frac{[(^{45}\text{Ca count in the medium})]}{[(^{45}\text{Ca count in the medium})] + [(^{45}\text{Ca count in the bone})]} \times 100$$

For control, bone fractions from fetuses of the same litter were cultured for two days in the absence of the test compound. The mean q standard deviation for the values from five bone fragments in each group were calculated, and their percent ratios to the control were calculated. The results are given in Table 2.

TABLE 2

| Compound (Example No.) | Concentration of Compound | Bone Resorption Inhibitory Activity [$^{45}$Ca Release Rate (Percent to Control)] |
|---|---|---|
| 3 | 10 μg/ml | 49 |
| 26 | 10 μM | 79 |
| 38 | 10 μM | 76 |
| 59 | 10 μM | 67 |
| 84 | 10 μM | 74 |
| 103 | 10 μg/ml | 49 |
| 108 | 10 μg/ml | 42 |
| 109 | 10 μg/ml | 38 |
| 110 | 10 μg/ml | 46 |
| 111 | 10 μg/ml | 32 |
| 112 | 10 μg/ml | 43 |
| 122 | 10 μM | 73 |
| 124 | 10 μM | 79 |
| 128 | 10 μM | 73 |
| 132 | 10 μM | 74 |
| 134 | 10 μM | 66 |
| 135 | 10 μM | 45 |
| 144 | 10 μM | 60 |
| 153 | 10 μM | 74 |
| 157 | 10 μM | 72 |
| 158 | 10 μM | 65 |

EXAMPLES

Reference Example 1

A mixture of N-benzyloxycarbonyl-(L)-isoleucyl-(L)-tryptophan methyl ester (11.3 g), palladium-carbon (5%, 50% wet, 3.0 g) and THF (50 ml) was subjected to catalytic hydrogenation at room temperature and atomospheric pressure. After the catalyst was filtered off, the filtrate was concentrated under reduced pressure to yield an oily substance. The oil was dissolved in N,N-dimethylformamide (50 ml), and 1-naphthalenesulfonyl chloride (5.8 g) and 4-(N,N-dimethylamino)pyridine (DMAP) (3.2 g) were added to the ice-cooling mixture. After stirring at 0° C. for 3 hours, the reaction mixture was concentrated under reduced pressure. The residue was suspended in ethyl acetate and the mixture was successively washed with 10% aqueous citric acid solution, water, saturated aqueous sodium hydrogen carbonate and brine, and dried (MgSO$_4$). The organic solvent was evaporated off to yield N-(1-naphthylsulfonyl)-(L)-isoleucyl-(L)-tryptophan methyl ester (9.8 g, 77%) as crystals. Melting point: 172–174° C.

Reference Example 2

To an ice-cooled mixture of N-(1-naphthylsulfonyl)-(L)-isoleucyl-(L)-tryptophan methyl ester (6.9 g) and THF (40 ml)-methanol (20 ml) was added dropwise a solution of KOH (1.5 g) in water (10 ml). After stirring at 0° C. for 20 hours, the reaction mixture was acidified with 1N HCl (35 ml) with ice-cooling, diluted with water and extracted with ethyl acetate. The ethyl acetate layer was washed with brine and dried (MgSO$_4$). The organic solvent was evaporated off to yield N-(1-naphthylsulfonyl)-(L)-isoleucyl-(L)-tryptophan (6.6 g, 98%) as crystals. Melting point: 167–168° C.

Reference Example 3

To a stirred solution of p-nitrobenzyl chloride (15 g) and diethyl benzylmalonate (22 g) in N,N-dimethylformamide (150 ml) was added NaH (60% in oil, 3.8 g). After stirring at room temperature for 2 days, the reaction mixture was concentrated under reduced pressure and the residue was suspended in ethyl acetate. The ethyl acetate layer was washed with aqueous citric acid solution, water, saturasted aqueous sodium hydrogen carbonate solution and brine, and dried (MgSO$_4$). The organic solvent was evaporated off and the residual oil was purified by column chromatography on silica gel. Elution with ethyl acetate-hexane (1:6, v/v) gave diethyl benzyl-4-nitrobenzylmalonate (24 g, 71%) as crystals. Melting point: 70–71°C.

Reference Example 4

A mixture of diethyl benzyl-4-nitrobenzylmalonate (24 g), KOH (14 g) and water (100 ml)-ethanol (150 ml) was stirred at 90–100° C. for 7 hours. The reaction mixture was concentrated under reduced pressure and the residue was acidified with 1N HCl and extracted with ethylacetate. The ethyl acetate layer was washed with brine, dried (MgSO$_4$) and concentrated under reduced pressure. The residue was dissolved in pyridine (100 ml) and the solution was stirred at 90° C. for 16 hours. The organic solvent was evaporated off and the residue was acidified with 1N HCl and extracted with ethyl acetate. The ethyl acetate layer was washed with brine, dried (MgSO$_4$) and concentrated under reduced pressure. The residual oil was purified by column chromatography on silica gel. Elution with ethyl acetate-hexane (1:3, v/v) gave 2-benzyl-3-(p-nitrophenyl)propionic acid (10.5 g, 59%) as crystals. Melting point: 104–105° C.

Reference Example 5

2-Benzyl-3-(p-nitrophenyl)propionic acid was converted to N-[2-benzyl-3-(p-nitrophenyl)propionyl]-(L)-tryptophanol by the method described for Example 1. Amorphous solid. $[\alpha]_D$:−12.5° (c 0.78, CHCl$_3$).

NMR (δ ppm in CDCl$_3$): 2.3–3.1 (7H,m), 3.2–3.4 (2H,m), 3.9–4.1 (1H,m), 5.20 & 5.34 (1H, each d,J=7.2 Hz), 6.58 &

6.62 (1H, each d,J=2.0 Hz), 7.0–7.4 (11H,m),7.92 & 8.02 (2H, each d,J=8.2 Hz), 8.04 (1H, broad s) Elemental analysis (for $C_{27}H_{27}N_3O_4 \cdot 1/4H_2O$) Calculated: C, 70.19; H, 6.00; N, 9.09 Found: C, 70.00; H, 6.25; N, 8.88

Reference Example 6

A mixture of diethyl 4-aminobenzylphosphonate (10 g) and diethyl benzylmalonate (24 g) was stirred at 160° C. for 24 hours. After cooling, the reaction mixture was purified by column chromatography on silica gel. Elution with chloroform-methanol (100:1, v/v) gave ethyl 2-(p-diethoxyphosphorylmethylphenylaminocarbonyl)-3-phenylpropionate (8.3 g, 45%) as crystals. Recrystallization from ethyl acetate-hexane gave colorless crystals having melting point of 115 to 116° C.

Reference Example 7

To an ice-cooled and stirred solution of ethyl 2-(p-diethoxyphosphorylmethylphenylaminocarbonyl)-3-phenylpropionate (6.0 g) in THF (30 ml)-ethanol (10 ml) was added dropwise a solution of KOH (0.9 g) in water (10 ml). After stirring at 4° C.-room temperature for 15 hours, the reaction mixture was acidified with 1N HCl, diluted with water and extracted with ethyl acetate. The ethyl acetate layer was washed with brine and dried (MgSO$_4$). The organic solvent was evaporated off to yield 2-(p-diethoxyphosphorylmethylphenylaminocarbonyl)-3-phenylpropionic acid (5.3 g, 94%) as crystals. Recrystallization from ethyl acetate-hexane gave pale yellow needles having melting point of 160 to 161° C.

Reference Example 8

To an ice-cooled and stirred solution of N-(2-ethoxycarbonyl-3-phenylpropionyl)-(L)-tryptophanol (15 g) in THF (40 ml)-methanol (30 ml) was added dropwise a solution of KOH (2.5 g) in water (10 ml). After stirring at 4° C.-room temperature for 20 hours, the reaction mixture was acidified with 1N HCl, diluted with water and extracted with ethyl acetate. The ethyl acetate layer was washed with brine and dried (MgSO$_4$). The organic solvent was evaporated off to yield N-(2-carboxy-3-phenylpropionyl)-(L)-tryptophanol (13.5 g, 97%) as crystals. Recrystallization from ethyl acetate-hexane gave pale yellow crystals having melting point of 130 to 131° C.

Example 1

A mixture of N-benzyloxycarbonyl-(L)-tryptophanol (0.974 g) in methanol (10 ml), palladium-carbon (10%, 0.195 g) was subjected to catalytic hydrogenation at room temperature under 1 atmospheric pressure. After the palladium-carbon was filtered off, the filtrate was concentrated under reduced pressure to yield an oily substance. This oily substance and N-benzyloxycarbonyl-(L)-phenylalanine (0.90 g) were dissolved in tetrahydrofuran (THF) (20 ml), and 1-hydroxybenzotriazole (HOBt) (0.506 g) and 1-ethyl-3-(3-dimethylaminopropyl)carbodiimide hydrochloride (WSCD.HCl) (0.69 g) were added at 0° C. After stirring at room temperature for 21 hours, the reaction mixture was poured over ethyl acetate. The ethyl acetate layer was washed by sequential additions of a 10% aqueous citric acid solution, a saturated aqueous sodium hydrogen carbonate solution and saturated saline and then dried (MgSO$_4$). After the solvent was distilled off, the oily residue was subjected to silica gel column chromatography and eluted with ethyl acetate-hexane (2:1) to yield N-benzyloxycarbonyl-(L)-phenylalanyl-(L)-tryptophanol (0.878 g, 62%).

Melting point: 154–156° C. $[\alpha]_D = -24.2°$ (c 0.24, DMSO) Elemental analysis (for $C_{28}H_{29}N_3O_4 \cdot 0.2H_2O$) Calculated: C, 70.78; H, 6.24; N, 8.84 Found: C, 70.86; H, 6.25; N, 8.70

Examples 2 through 11

The same procedure as in Example 1 was followed to yield the compounds listed in Table 3.

TABLE 3

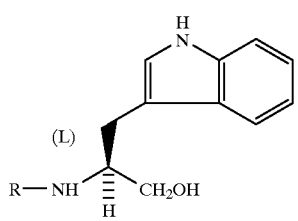

| Example No. | R | Melting Point (° C.) | Recrystallization Solvent | Optical Rotation $[\alpha]_D$ (c, solvent) |
|---|---|---|---|---|
| 2 | tBuOCO—Ile— | 105–108 | Ethyl acetate-hexane | −31.5° (c 0.375, CHCl$_3$) |
| 3 | 1-Nap—SO$_2$—Ile— | 150–151 | CH$_2$Cl$_2$-ether | −77.7° (c 0.57, CHCl$_3$) |
| 4 | 4-Tol—SO$_2$—Phe— | 159–160 | Ethyl acetate-hexane | −6.3° (c 0.485, DMSO) |
| 5 | 1-Nap—SO$_2$—Gly— | Note[1] | — | −9.2° (c 0.50, CHCl$_3$) |
| 6 | PhCH$_2$OCO—Ile—Ile— | 184–185 | Tetrahydrofuran-hexane | −40.0° (c 0.145, DMSO) |
| 7 | PhCH$_2$OCO—Ile— | 184–185 | Ethyl acetate-hexane | −40.0° (c 0.50, DMSO) |
| 8 | tBuOCO—Ile—Ile— | Note 2) — | — | −19.4° (c 0.17, DMSO) |
| 9 | 1-Nap—SO$_2$—Ile—Ile— | 170–172 | Ethyl ether | −37.5° (c 0.2, DMSO) |

TABLE 3-continued

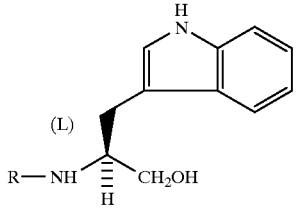

| Example No. | R | Melting Point (° C.) | Recrystallization Solvent | Optical Rotation [α]$_D$ (c, solvent) |
|---|---|---|---|---|
| 10 | CH$_3$OCO(CH$_2$)$_2$CO— Ile—Ile— | 213–214 | Tetrahydrofuran-hexane | |
| 11 | 1-Ada—(CH$_2$)$_2$OCO— Ile—Ile— | Note[3] | — | |

Ile: (L)-isoleucine, Phe: (L)-phenylalanine, Gly: glycine, tBu: tert-butyl, 1-nap:(1)-naphthyl, 4-Tol: 4-tolyl, Ph: phenyl, 1-Ada: adamantan-1-yl Note 1) Amorphous solid
NMR (δ ppm in CDCl$_3$): 2.69 (2H, dd, J=4 & 6 Hz), 3.35 (2H, d, J=6 Hz), 3.25–3.49 (3H, m), 4.06–4.14 (1H, m), 6.32 (1H, t, J=6 Hz), 6.71 (1H, d, J=8.0 Hz), 6.92 (1H, d, J=2 Hz), 7.04 (1H, dt, J=1 & 7 Hz), 7.13 (1H, dt, J=1 & 7 Hz), 7.26 (1H, d, J=8 Hz),7.39 (1H, t, J=8 Hz),7.49 (1H, d, J=10 Hz), 7.50 (2H, dd, J=7 & 9 Hz), 7.86 (1H, dd, J=3 & 7 Hz), 7.96 (1H, d, J=8 Hz), 8.11 (1H, dd, J=1 & 7 Hz), 8.27 (1H, d, J=2 Hz), 8.50 (1H, dd, J=3 & 6 Hz)

Note 2) Amorphous solid
NMR (δ ppm in d$_6$-DMSO): 0.76–0.82 (12H, m), 1.00–1.18 (2H, m), 1.28–1.47 (2H, m), 1.37 (9H, s), 1.60–1.75 (2H, m), 2.67–2.96 (2H, m), 3.31–3.36 (2H, m), 3.77–3.85 (1H, m), 3.93–4.04 (1H, m), 4.13–4.22 (1H, m), 4.65 (1H, t, J=5.2 Hz), 6.87–7.09 (4H, m), 7.32 (1H, d, J=7.4 Hz), 7.59–7.78 (3H, m), 10.75 (1H, br s). SI-MS m/z: 517 (MH$^+$).

Note 3) Amorphous solid
NMR (δ ppm in d$_6$-DMSO): 0.74–0.83 (12H, m), 0.98–1.16 (2H, m), 1.28–1.90 (21H, m), 2.68–2.95 (2H, m), 3.25–3.42 (2H, m), 3.83–4.21 (5H, m), 4.65 (1H, t, J=5.6 Hz), 6.92–7.16 (4H, m), 7.31 (1H, d, J=7.4 Hz), 7.62 (1H, d, J=7.0 Hz), 7.69–7.75 (2H, m), 10.74 (1H, br s). SI-MS m/z: 623 (MH$^+$).

Example 12

The same procedure as in Example 1 was followed to yield N-(1naphthylsulfonyl)-(L)-isoleucyl-(L)-isoleucyl-(DL)-(1-naphthyl)alaninol, which was recrystallized from ethyl acetate. Melting point: 198–200° C.

Example 13

A mixture of N-benzyloxycarbonyl-(L)-isoleucyl-(L)-tryptophanol(2.14 g), palladium-carbon (5%, 50% wet, 1.0 g) and methanol-THF (5:1, 30 ml) was subjected to catalytic hydrogenation at room temperature and atomospheric pressure. After the catalyst was filtered off, the filterate was concentrated under reduced pressure to yield an oily substance. The oil and valproic acid (0.71 g) were dissolved in N,N-dimethylformamide (20 ml), and 1-hydroxybenzotriazole (HOBt) (0.82 g) and a solution of 1-ethyl-3-(3-dimethylaminopropyl)carbodiimide hydrochloride (WSCD·HCl)(1.13 g) in dichloromethane (20 ml) were added thereto at 0° C. After stirring at 0° C. for 1 hour and at room temperature for 15 hours, the reaction mixture was concentrated under reduced pressure and the residue was suspended in ethyl acetate (120 ml). The mixture was successively washed with 10% aqueous citric acid solution, water, saturated aqueous sodium hydrogen carbonate and brine, and dried (MgSO$_4$). The organic solvent was evaporated off to yield N-valproyl-(L)-isoleucyl-(L)-tryptophanol (1.78 g, 84.8%) as crystals. Recrystallization from ethyl acetate-hexane gave colorless needles.

Melting point: 190–191° C. [α]$_D$=−60.8° (c 0.50, CH$_3$OH) Elemental analysis (for C$_{25}$H$_{39}$N$_3$O$_3$) Calculated: C,69.90; H,9.15; N,9.78 Found: C,69.69; H,9.14; N,9.50

Example 14

A mixture of N-benzyloxycarbonyl-(L)-tryptophanol (1.0 g) in ethanol hydrogenation (20 ml)-dioxane (40 ml), palladium-carbon (5%, 0.5 g) was subjected to catalytic hydrogenation at room temperature under 1 atmospheric pressure. After the palladium-carbon was filtered off, the filtrate was concentrated under reduced pressure to yield an oily substance. This oily substance was dissolved in N,N-dimethylformamide (10 ml), and 1-naphthalenesulfonyl chloride (0.77 g) was added and then triethylamine (0.39 g) was added at 0° C. After overnight stirring at room temperature, the reaction mixture was poured over water and extracted with ether. The ether layer was washed by sequential additions of a 10% aqueous citric acid solution, a saturated aqueous sodium hydrogen carbonate solution and saturated saline and then dried (MgSO$_4$). After the solvent was distilled off, the oily residue was subjected to silica gel column chromatography and eluted with ethyl acetate-hexane (1:1) to yield a powder of N-(1-naphthylsulfonyl)-(L)-tryptophanol (0.8 g, 68%).

Melting point: 85–87° C. [α]$_D$=−104.9° (c 0.5, CHCl$_3$)

Example 15

A solution of N-benzyloxycarbonyl-(DL)-α-naphthylalanine (6.0 g) in ethyl acetate (200 ml) was treated with a solution of diazomethane in ether to yield N-benzyloxycarbonyl-(DL)-α-naphthylalanine methyl ester as an oily substance. This oily substance was dissolved in ethanol (60 ml)-tetrahydrofuran (THF) (40 ml), and sodium borohydride (1.3 g) and lithium chloride (LiCl) (1.5 g) were added under an argon stream. After stirring at room temperature for 1 hour, the reaction mixture was concentrated under reduced pressure, and the residue poured over ethyl acetate. The ethyl acetate layer was washed by sequential additions of a saturated aqueous sodium hydrogen carbonate solution and saturated saline and then dried (MgSO$_4$). The solvent was distilled off to yield N-benzyloxycarbonyl-(DL)-α-naphthylalaninol (5.3 g, 91%) as a colorless solid.

$^1$H-NMR (δ ppm in CDCl$_3$): 3.29 (1H,dd,J=8.2&12.8 Hz), 3.42 (1H,dd,J=7.2&12.8 Hz), 3.5–3.8 (2H,m), 4.0–4.2 (1H,m), 5.11 (2H,s), 7.3–7.9 (12H,m), 8.21 (1H,d,J=7.2 Hz)

Example 16

A mixture of N-benzyloxycarbonyl-(L)-isoleucyl-(L)-tryptophanol (55 g), palladium-carbon (5%, 50% wet, 30 g) and ethanol (50 ml)-THF (300 ml) was subjected to catalytic hydrogenation at room temperature and atomospheric pressure. After the catalyst was filtered off, the filterate was concentrated under reduced pressure to yield an oily substance. The oil was dissolved in N,N-dimethylformamide (300 ml), and 1-naphthalenesulfonyl chloride (30 g) and 4-(N,N-dimethylamino)pyridine (DMAP) (17 g) were added to the ice-cooling mixture. After stirring at 0° C. for 2 hours, the reaction mixture was concentrated under reduced pressure. The residue was suspended in ethyl acetate and the mixture was successively washed with 10% aqueous citric acid solution, water, saturated aqueous sodium hydrogen carbonate and brine, and dried (MgSO$_4$). The organic solvent was evaporated off and the residual oil was purified by column chromatography on silica gel. Elution with ethyl acetate-hexane (3:2, v/v) gave N-(1-naphthylsulfonyl)-(L)-isoleucyl-(L)-tryptophanol (51 g, 82%) as crystals.

Example 17

To a solution, being ice cooled, of N-tert-butoxycarbonyl-(L)-isoleucyl-(L)-tryptophanol (1.0 g) in chloroform (10 ml), trifluoroacetic acid (5%, 0.5 g) was added, followed by stirring at the same temperature for 4 hours. After the reaction mixture was concentrated under reduced pressure, ethyl acetate was added to the residue. The ethyl acetate layer was washed with water and dried (MgSO$_4$), and the solvent was distilled off to yield (L)-isoleucyl-(L)-tryptophanol as an oily substance. This oily substance was dissolved in chloroform (20 ml), and p-toluenesulfonyl chloride (0.52 g) was added and then triethylamine (1.4 ml) was added at 0° C. After stirring at room temperature for 2 days, the reaction mixture was poured over water and extracted with chloroform. After the chloroform layer was dried (MgSO$_4$), the solvent was distilled off, and the oily residue was recrystallized from ethyl acetate to yield N-(p-toluenesulfonyl)-(L)-isoleucyl-(L)-tryptophanol (0.32 g, 28%).

Melting point: 217–219° C. $[\alpha]_D$=–32.7° (c 0.695, CH$_3$OH)

Example 18

A mixture of N-benzyloxyearbonyl-(L)-isoleucyl-(L)-tryptophanol (0.7 g) in ethanol (30 ml)-tetrahydrofuran (20 ml), palladium-carbon (5%, 0.5 g) was subjected catalytic hydrogenation at room temperature under 1 atmospheric pressure. After the palladium-carbon was filtered off, the filtrate was concentrated under reduced pressure to yield an oily substance. This oily substance was dissolved in dichloromethane (15 ml)-tetrahydrofuran (5 ml), and m-methylphenyl isocyanate (0.225 g) was added at 4° C. After stirring at room temperature for 1.5 hours, the reaction mixture was poured over chloroform-methanol. After the insoluble substances were filtered off, the filtrate was concentrated under reduced pressure, and the residual solid was recrystallized from dichloromethane-methanol-hexane to yield N-(3-methylphenylcarbamoyl)-(L)-isoleucyl-(L)-tryptophanol (0.43 g, 61%).

Melting point: 185–186° C. Elemental analysis (for C$_{25}$H$_{32}$N$_4$O$_3$) Calculated: C, 68.78; H, 7.39; N, 12.83 Found: C, 68.35; H, 7.41; N, 12.91

Example 19

The same procedure as in Example 18 was followed to yield N-benzylcarbamoyl-(L)-isoleucyl-(L)-tryptophanol.

Melting point: 132–133° C. $[\alpha]_D$=–42.9° (c 0.34, DMSO)

Example 20

The same procedure as in Example 18 was followed to yield N-[(2-cyclohexylethyl)carbamoyl]-(L)-isoleucyl-(L)-tryptophanol.

Melting point: 182–184° C. $[\alpha]_D$=–27.7° (c 0.37, DMSO)

Example 21

The same-procedure as in Example 18 was followed to yield N-isopropylcarbamoyl-(L)-isoleucyl-(L)-tryptophanol.

Melting point: 211–213° C.

Example 22

The same procedure as in Example 18 was followed to yield N-[(2-trifluoromethylphenyl)carbamoyl]-(L)-isoleucyl-(L)-tryptophanol.

Melting point: 232–234° C.

Examples 23 through 53

The same procedure as in Examples 1, 16 and 18 was followed to yield the compounds listed in Table 4.

TABLE 4

Structure: L-tryptophanol derivative with R—NH—CH(CH₂-indol-3-yl)—CH₂OH (L configuration)

| Example No. | R | Melting Point (° C.) | Recrystallization Solvent | Optical Rotation [α]_D (c, solvent) | Procedure followed (Example No.) |
|---|---|---|---|---|---|
| 23 | PhCH₂OCO—Gly— | 87–88 | Ethyl acetate-ether | −15.0° (0.50, CHCl₃) | 1 |
| 24 | tBuOCO—Phe— | 150–151 | Ethyl acetate-hexane | −20.2° (0.96, CHCl₃) | 1 |
| 25 | 1-Nap—SO₂—Phe— | —¹⁾ | Ethyl acetate-hexane | −113.3° (0.86, CHCl₃) | 16 |
| 26 | (PhCH₂)₂CHCO— | 120–121 | — | −13.9° (0.62, CHCl₃) | 1 |
| 27 | PhCH₂CH₂CO— | 134–135 | Ethyl acetate-hexane | −14.5° (0.54, CHCl₃) | 1 |
| 28 | 1-Nap—SO₂—Ala— | —²⁾ | | −77.5° (0.50, CHCl₃) | 16 |
| 29 | (C₃H₇)₂CHCO—Ala— | 144–145 | Ethyl acetate-hexane | −64.7° (0.50, CH₃OH) | 13 |
| 30 | PhCH₂OCO—Trp— | 105–106 | Ethyl acetate-ether | −43.4° (1.05, DMSO) | 1 |
| 31 | tBuOCO—Trp— | 120–122 | Ethyl acetate-ether | −39.7° (0.62, DMSO) | 1 |
| 32 | PhCO—Phe— | 165–167 | DMF—H₂O | −46.3° (0.745, DMSO) | 1 |
| 33 | (PhS)(C₃H₇)CHCO— | 141–142 | Ethyl acetate | +66.6° (0.55, CHCl₃) | 1 |
| 34 | PhCH₂NHCS—Ile— | —³⁾ | Ethyl acetate-ether | <40.4° (0.255, DMSO) | 18 |
| 35 | 1-Nap—NHCO—Ile— | 217–218 | Ethyl acetate-methanol | −5.6° (0.325, DMSO) | 18 |
| 36 | PhCH₂OCO—Val— | 163–164 | Ethyl acetate-hexane | −43.3° (0.50, CH₃OH) | 1 |
| 37 | 1-Nap—SO₂—Val— | —⁴⁾ | | −28.8° (0.50, CH₃OH) | 16 |
| 38 | PhCO—Val— | 173–174 | Ethyl acetate-hexane | −35.80 (0.50, CH₃OH) | 1 |
| 39 | (C₃H₇)₂CHCO—Val— | 187–188 | Ethyl acetate-hexane | −63.8° (0.50, CH₃OH) | 13 |
| 40 | (2-benzimidazolyl-S)(C₃H₇)CHCO— | 165–167 | Ethyl acetate-hexane | −52.1° (0.53, CH₃OH) | 1 |
| 41 | PhNHCS—Ile— | —⁵⁾ | — | −26.9 (0.295, CHCl₃) | 18 |
| 42 | 1-Nap—NHCS—Ile— | —⁶⁾ | — | −11.7° (0.43, CHCl₃) | 16 |
| 43 | PhCO—Gly— | 149–150 | Ethyl acetate-hexane | −16.3° (0.50, CH₃OH) | 1 |
| 44 | PhCH₂OCO—Ala— | 158–159 | Ethyl acetate-hexane | −40.1° (0.50, CH₃OH) | 1 |
| 45 | PhCH₂OCO—Leu— | 103–104 | Ethyl acetate-hexane | −46.1° (0.50, CH₃OH) | 1 |
| 46 | 1-Nap—SO₂—Leu— | —⁷⁾ | — | −100.7° (0.50, CHCl₃) | 16 |
| 47 | PhCO—Leu— | 200–201 | Ethyl acetate | −39.5° (0.50, CH₃OH) | 1 |
| 48 | (C₃H₇)₂CHCO—Leu— | 149–150 | Ethyl acetate-hexane | −64.8° (0.50, CH₃OH) | 13 |
| 49 | (C₃H₇)₂CHCO—Gly— | 177–178 | Ethyl acetate-hexane | −13.2° (0.50, CH₃OH) | 13 |
| 50 | PhCO—Ile— | 142–143 | Ethyl acetate-hexane | −27.2° (0.26, CHCl₃) | 1 |
| 51 | Ph(CH₂)₃CO— | 99–100 | Ethyl acetate-hexane | −15.5° (0.435, CHCl₃) | 1 |
| 52 | (C₃H₇)₂CHCO—Phe— | 191–192 | Ethyl acetate-hexane | −34.3° (0.50, CH₃OH) | 13 |
| 53 | (C₃H₇)₂CHCO— | 153–154 | CHCl₃-ethanol-isopropyl ether | −19.8° (0.50, CHCl₃) | 1 |

Ile: (L)-isoleucine, Leu: (L)-leucine, Ala: (L)-alanine, Gly: glycine, Val: (L)-valine, Trp: (L)-tryptophan, Phe: (L)-phenylalanine, Note 1) Amorphous solid NMR (δ ppm in CDCl$_3$): 2.45 (1H,m), 2.58–3.00 (4H,m), 3.50 (1H,m), 3.72 (1H,m), 4.19 (1H,m), 5.00 (1H,m), 6.48 (1H,m), 6.60–6.70 (2H,m), 7.06–7.59 (6H,m), 7.87–8.21 (5H,m).

Note 2) Amorphous solid

NMR (δ ppm in CDCl$_3$): 0.93 (3H,d,J=7 Hz), 2.69–2.80 (1H,m), 2.74 (1H,dd,J=7&4 Hz), 2.90 (1H,dd,J=7&15 Hz), 3.34–3.52 (2H,m), 3.64 (1H,quintet,J=7 Hz), 4.10–4.14 (1H,m), 5.45 (1H,,d,J=7 Hz), 6.61 (1H,d,J=8 Hz), 7.00 (1H,d,J=2 Hz), 7.11 (1H,dt,J=1&8 Hz), 7.20 (1H,dt,J=8 Hz), 7.34 (1H,dd,J=1&7 Hz), 7.47 (1H,dt,J=8&7 Hz), 7.56 (2H,dd,J=1&8 Hz), 7.58–7.68 (1H,m), 7.92–7.97 (1H,m), 8.06 (1H,d,J=8 Hz) 8.20 (1H,dd,J=1&7 Hz), 8.22 (1H,s); 8.53 (1H,dd,J=2&8 Hz).

Note 3) Amorphous solid

NMR (δ ppm in CDCl$_3$): 0.7–1.2 (7H,m), 1.3–1.6 (1H,m), 1.7–2.0 (1H,m), 2.3–2.5 (1H,m), 2.85 (2H,d,J=6.2 Hz), 3.3–3.6 (2H,m), 3.9–4.1 (1H,m), 4.4–4.6 (1H,m), 4.71 (2H, broad d,J=8.4 Hz), 6.63 (1H,broad d,J=8.0 Hz), 7.00 (1H,d,J=1.8 Hz), 7.1–7.4 (8H,m), 7.56 (1H,d,J=7.4 Hz), 8.10 (1H,s).

Note 4) Amorphous solid

NMR (δ ppm in CDCl$_3$): 0.50 (6H,t,J=7 Hz), 1.92–2.03 (1H,m), 2.48–2.54 (1H,m), 2.62 (1H,dd,J=7&15 Hz), 2.80 (1H,1dd,J=7&15 Hz), 3.39 (2H,dd,J=5&7 Hz), 4.03–4.09 (1H,m), 5.40 (1H,d,J=7 Hz), 6.32 (1H,d,J=8 Hz), 6.98 (1H, d,J=2 Hz), 7.12 (1H,dt,J=1&7 Hz), 7.20 (1H,dt,J=1&7 Hz), 7.34 (1H,d,J=7 Hz), 7.47 (1H,dd,J=7&8 Hz), 7.53 (1H,d,J=8 Hz), 7.60 (1H,dd,J=1&8 Hz), 7.68 (1H,ddd,J=2&7&8 Hz), 7.92 (1H,dd,J=1&7 Hz), 8.66 (1H,d,J=9 Hz).

Note 5) Amorphous solid

NMR (δ ppm in CDCl$_3$): 0.7–1.1 (7H,m), 1.2–1.5 (1H,m), 1.8–2.0 (1H,m), 2.80 (1H,t,J=5.4 Hz), 3.00 (2H,d,J=6.8 Hz), 3.5–3.8 (2H,m), 4.2–4.4 (1H,m), 4.78 (1H,t,J=7.4 Hz), 6.47 (1H,d,J=7.8 Hz), 6.71 (1H,d,J=8 .0 Hz), 7.0–7.4 (9H,m), 7.61 (1H,d,J=7.4 Hz), 8.23 (1H,broads), 8.26 (1H,d,J=10.0 Hz).

Note 6) Amorphous solid

NMR (δ ppm in CDCl$_3$): 0.6–0.9 (7H,m), 1.0–1.3 (1H,m), 1.6–1.9 (1H,m), 2.73 (1H,t,J=6.2 Hz), 2.9–3.1 (2H,m), 3.5–3.8 (2H,m). 4.1–4.3 (1H,m), 4.74 (1H,t,J=7.8 Hz), 6.17 (1H,d,J=8.0 Hz), 6.36 (1H,d,J=7.8 Hz), 7.0–8.0 (12H,m), 8.16 (1H, broad s), 8.22 (1H, broad s).

Note 7) Amorphous solid

NMR (δ ppm in CDCl$_3$): 0.16 (3H,d,J=6 Hz), 0.56 (3H,d,J=6 Hz), 1.04–1.19 (2H,m), 1.25–1.34 (1H,m), 2.68–2.79 (1H,m), 2.73 (1H,dd,J=7&15 Hz), 2.89 (1H,dd,J=7&14 Hz), 3.35–3.56 (3H,m), 4.07–4.18 (1H,m), 5.39 (1H,d,J=6 Hz), 6.55 (1H,d,J=8 Hz), 7.03 (1H,d,J=2 Hz), 7.12 (1H,dt,J=1&7 Hz), 7.21 (1H,dt,J=1&7 Hz), 7.36 (1H,d,J=7 Hz), 7.49 (1H,dd,J=7&8 Hz), 7.58 (1H,d,J=7 Hz), 7.59 (1H,dt,J=2&7 Hz), 7.68 (1H,dt,J=2&7 Hz), 7.95 (1H,dd,J=2&8 Hz), 8.07 (1H,d,J=8 Hz), 8.22 (1H,d,J=1 Hz), 8.24 (1H,dd,J=1&7 Hz), 8.61 (1H,d,J=8 Hz).

Examples 54 through 68

The same procedure as in Example 1 and 16 was followed to yield the compounds listed in Table 5.

TABLE 5

$$R^4-NH-\overset{(L)}{\underset{H}{C}}-CONH-\overset{R^1\;(L)}{\underset{H}{C}}-CH_2OH$$

| Example No. | R$^4$ | R$^1$ | Melting Point (° C.) | Recrystallization Solvent | Optical Rotation [α]$_D$ (c, solvent) | Procedure followed (Example No.) |
|---|---|---|---|---|---|---|
| 54 | tBuOCO— | —CH$_2$-(N-CH$_3$ indole) | 132–133 | CH$_2$Cl$_2$-Ethyl acetate-hexane | −25.7° (0.34, DMSO) | 1 |
| 55 | PhCH$_2$OCO— | —CH$_3$ | 156–157 | methanol CH$_2$Cl$_2$—hexane | +2.3° (0.375, DMSO) | 1 |
| 56 | PhCH$_2$OCO— | —CH$_2$Ph | 164–165 | methanol-ethyl acetate | −38.0° (0.27, DMSO) | 1 |
| 57 | 1-Nap—SO$_2$— | —CH$_3$ | 178–179 | Ethyl acetate-hexane | +54.3° (0.38 DMSO) | 16 |
| 58 | 1-Nap—SO$_2$— | —CH$_2$Ph | 169–170 | Ethyl acetate-hexane | −108.3° (0.65, CHCl$_3$) | 16 |

TABLE 5-continued $$R^4-NH-\underset{H}{\overset{(L)}{C}}(sBu)-CONH-\underset{H}{\overset{R^1\ (L)}{C}}-CH_2OH$$

| Example No. | $R^4$ | $R^1$ | Melting Point (° C.) | Recrystallization Solvent | Optical Rotation $[\alpha]_D$ (c, solvent) | Procedure followed (Example No.) |
|---|---|---|---|---|---|---|
| 59 | PhCH₂OCO— | —CH₂-(1-(C(CH₃)₃)-indol-3-yl) | 117–118 | Ethyl acetate-hexane | −22.6° (0.295, CHCl₃) | 1 |
| 60 | PhCH₂OCO— | —CH₂-C₆H₄-OH (para) | 188–189 | Ethyl acetate-hexane | −34.0° (0.355, DMSO) | 1 |
| 61 | PhCH₂OCO— | —CH₂-C₆H₄-OCH(CH₃)₂ (para) | 174–175 | Ethyl acetate-hexane | −34.0° (0.38, DMSO) | 1 |
| 62 | 1-Nap—SO₂— | —CH₂-C₆H₄-OH (para) | 204–205 | Ethyl acetate-hexane | −9.3° (0.36, DMSO) | 16 |
| 63 | 1-Nap—SO₂— | —CH₂-C₆H₄-OCH(CH₃)₂ (para) | 130–131 | Ethyl acetate-hexane | −92.3° (0.34, CHCl₃) | 16 |
| 64 | PhCH₂OCO— | —CH(CH₃)₂ | 149–150 | Ethyl acetate | −36.7° (0.37, CHCl₃) | 1 |
| 65 | PhCH₂OCO— | —CH₂CH(CH₃)₂ | 151–153 | Ethyl acetate-hexane | −34.1° (0.36, CHCl₃) | 1 |
| 66 | 1-Nap—SO₂— | —CH(CH₃)₂ | 159–160 | Ethyl acetate | +8.0° (0.26, CHCl₃) | 16 |
| 67 | 1-Nap—SO₂— | —CH₂CH(CH₃)₂ | 88–89 | Ethyl acetate-hexane | +28.5° (0.265, DMSO) | 16 |
| 68 | PhCH₂OCO— | H | 160–161 | Ethyl acetate-hexane | −4.9° (0.50, CHCl₃) | 1 |

DMSO: dimethyl sulfoxide, Ph: phenyl, 1-Nap: 1-naphthyl, tBu: tert. butyl

Examples 69 through 73

The same procedure as in Example 1 was followed to yield the compounds listed in Table 6.

TABLE 6

$$R-NH-\overset{R^1}{\underset{H}{\overset{|}{C}}}-CH_2OH \quad (L)$$

| Example No. | R | $R^1$ | Melting Point (° C.) | Recrystallization Solvent | Optical Rotation $[\alpha]_D$ (c, solvent) |
|---|---|---|---|---|---|
| 69 | $(PhCH_2)_2CHCO$— | —$CH_2Ph$ | 115–116 | $CH_2Cl_2$—hexane | −18.3° (0.56, $CHCl_3$) |
| 70 | $PhCH_2OCO$—Leu—Leu— | H | 112–113 | Ethyl acetate-hexane | −17.0° (0.305, DMSO) |
| 71 | $(PhCH_2)_2CHCO$— | —$CH_2CH_3$ | 161–162 | Ethyl acetate-methanol-hexane | −34.6° (0.54, $CHCl_3$) |
| 72 | $(PhCH_2)_2CHCO$— | —$CH(CH_3)_2$ | 148–149 | Ethyl acetate-hexane | −31.5° (0.50, $CHCl_3$) |
| 73 | $(PhCH_2)_2CHCO$— | —$CH_3$ | 144–145 | $CH_2Cl_2$—isopropyl ether-hexane | −17.9° (0.50, $CHCl_3$) |

Leu:(L) - leucine, Ph: phenyl

Example 74

The same procedure as in Example 1 was followed to yield N-benzyloxycarbonyl-(L)-isoleucyl-(D)-tryptophanol. m.p. 198–199° C. (recrystallized from ethyl acetate-hexane). $[\alpha]_D$=+31.8° (c 0.945, DMSO)

Example 75

The same procedure as in Example 16 was followed to yield N-(1-naphthylsulfonyl)-(L)-isoleucyl-(D)-tryptophanol as an amorphous solid. $[\alpha]_D$=−16.0° (c 0.34, $CHCl_3$)

NMR (δ ppm in $CDCl_3$): 0.4–0.9 (7H,m), 1.1–1.3 (1H,m), 1.5–1.7 (1H,m), 2.6–2.8 (1H,m), 2.74 (2H,d,J=7.0 Hz), 3.2–3.4 (2H,m), 3.45 (1H,dd,J=6.0&8.2 Hz), 3.9–4.2 (1H, m), 5.7–5.9 (1H,m), 6.1–6.3 (1H,m), 7.00 (1H,d,J=1.6 Hz), 7.0–7.7 (7H,m), 7.90 (1H,d,J=8.0 Hz), 7.99 (1H,d,J=8.4 Hz), 8.20 (2H,d,J=7.2 Hz), 8.67 (1H,d,J=8.2 Hz)

Examples 76 through 97

The same procedure as in Examples 1 and 13 was followed to yield the compounds listed in Tables 7 and 8.

TABLE 7

$$R^4-NH-\overset{R^1}{\underset{H}{\overset{|}{C}}}-CH_2OH \quad (L)$$

| Example No. | $R^4$ | $R^1$ | Melting Point (° C.) | Recrystallization Solvent | Optical Rotation $[\alpha]_D$ (c, solvent) | Procedure followed (Example No.) |
|---|---|---|---|---|---|---|
| 76 | $(C_3H_7)_2CHCO$— | $PhCH_2$— | 133–134 | $CH_2Cl_2$—ether-isopropyl ether | −25.4° (0.5, $CHCl_3$) | 1 |
| 77 | $Ph(CH_2)_3CO$— | $PhCH_2$— | 113–114 | AcOEt-ether-hexane | 22.80 (0.5, $CHCl_3$) | |
| 78 | $PhCH_2OCO$—Leu- | H | 126–127 | AcOEt-hexane | +11.6°[1]) (0.41, DMSO) | 1 |
| 79 | 1-Nap—$SO_2$—Leu—Trp— | H | 215–216 | AcOEt | −15.4° (0.24, DMSO) | 1 |

Leu: (L) - leucine, Trp: (L)-tryptophan, Ph: phenyl, 1-Nap: 1-naphthyl, AcOEt: ethyl acetate

[1])$[\alpha]_{Hg}$

TABLE 8

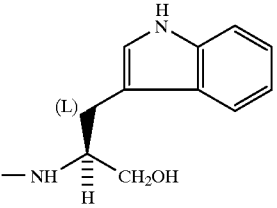

| Example No. | R | Melting Point (° C.) | Recrystallization Solvent | Optical Rotation [α]$_D$ (c, solvent) | Procedure followed (Example No.) |
|---|---|---|---|---|---|
| 80 | (CH$_3$)$_2$CHCH$_2$CH$_2$CO— | 114–115 | AcOEt-hexane | −19.0° (0.5, CH$_3$OH) | 1 |
| 81 | cyclohexyl-CO— | 164–165 | AcOEt-hexane | −20.8° (0.5, CH$_3$OH) | 1 |
| 82 | Ph—CO— | 129–130 | AcOEt-hexane | −74.4° (0.5, CH$_3$OH) | 1 |
| 83 | Ph(C$_2$H$_5$)CH—CO— | 103–104 | AcOEt-hexane | −22.4° (0.645, CHCl$_3$) | 1 |
| 84 | (PhCH$_2$)[(4-CH$_3$—C$_6$H$_4$)CH$_2$]CH—CO— | —[1] | | −16.0° (0.53, CHCl$_3$) | 1 |
| 85 | PhCH$_2$—CO—Val— | 197–198 | AcOEt-hexane | −60.7° C. (0.50, CH$_3$OH) | 13 |
| 86 | (PhCH$_2$)$_2$CH—CO—Val— | 157–158 | AcOEt-hexane | −48.3 (0.50, CH$_3$OH) | 13 |
| 87 | (PhCH$_2$)[(2-CH$_3$O—C$_6$H$_4$)CH$_2$]CH—CO— | 98–100 | | −17.5° (0.53, CHCl$_3$) | 1 |
| 88 | (PhCH$_2$)[(4-CH$_3$O—C$_6$H$_4$)CH$_2$]CH—CO— | —[2] | | −24.8° (0.59, CHCl$_3$) | 1 |
| 89 | [(4-PhCONH—C$_6$H$_4$)CH$_2$](PhCH$_2$)CH—CO— | 173–174 | AcOEt-hexane | −65.50 (0.535, CHCl$_3$) | —[6] |
| 90 | [(4-CH$_3$CONH—C$_6$H$_4$)CH$_2$](PhCH$_2$)CH—CO— | 114–115 | AcOEt-hexane | −18.2° (0.475, CHCl$_3$) | —[7] |
| 91 | [4-(4-Tol—SO$_2$NH)—C$_6$H$_4$CH$_2$](PhCH$_2$)CH—CO | 150–151 | AcOEt-hexane | −16.1° (0.815, DMSO) | —[8] |
| 92 | [[4-(C$_2$H$_5$O)$_2$P(O)CH$_2$]—C$_6$H$_4$NHCO](PhCH$_2$)CH—CO— | —[3] | | −37.1° | 1 |
| 93 | (C$_2$H$_5$OOC)(PhCH$_2$)CH—CO— | —[4] | | | 1 |
| 94 | [(PhCH$_2$)$_2$N—CO]—(PhCH$_2$)CHCO— | —[5] | | −21.8° (0.405, CHCl$_3$) | —[9] |
| 95 | (PhCH$_2$NH—CO)—(PhCH$_2$)CHCO— | 187–188 | AcOEt-hexane | −40.8° (0.83, DMSO) | —[10] |
| 96 | Ph$_2$CH—CO— | 207–209 | AcOEt-hexane | −24.8° (0.345, DMSO) | 1 |
| 97 | (4-oxo-4H-1-benzopyran-2-yl)-CO—Ile— | 164–165 | ethanol-hexane | −54.8° (0.53, CH$_3$OH) | 13 |

Leu: (L)-Ieucine, Val: (L)-valine, Ph: phenyl, 4-Tol: 4-tolyl, AcOEt: ethyl acetate Note 1) Amorphous solid
NMR (δ ppm in CDCl$_3$): 2.29&2.31 (3H,each s), 2.34–2.52 (1H,m), 2.60–3.08 (6H,m), 3.18–3.42 (2H,m), 3.93–4.11 (1H,m), 5.10–5.20 (1H,m), 6.42&6.50 (1H,each d,J=2.2 Hz), 7.00–7.40 (13H,m), 7.89–1H,broad).

Note 2) Amorphous solid
NMR (δ ppm in CDCl$_3$): 2.32–2.50 (1H,m), 2.60–3.07 (4H,m), 3.20–3.43 (2H,m), 3.75&3.78 (3H,each s), 3.92–4.15 (1H,m), 5.04–5.20 (1H,m), 6.31&6.43 (1H,each d,J=2.3 Hz), 6.79 (2H,d,J=8.5 Hz), 7.02–7.46 (9H,m), 7.87–8.00 (1H,broad).

Note 3) Amorphous solid
NMR (δ ppm in CDCl$_3$): 1.22 (3H,t,J=6.0 Hz), 1.23 (3H,t,J=6.0 Hz),2.70–3.60 (10H,m), 3.90–4.10 (4H,m), 4.1–4.30 (1H,m), 6.70&6.83 (1H,each d,J=2.2 Hz), 6.82&6.88 (1H,each d,J=8.0 Hz), 7.0–7.4 (12H,m), 7.52&7.58 (1H,each d,J=7.4 Hz), 5 8.37&8.46 (1H,each broad s), 9.29&9.31 (1H,each broad s).

Note 4) Oil
NMR (δ ppm in CDCl$_3$): 1.10&1.12 (3H,each t,J=7.0 Hz), 2.40–2.60 (1H,m), 2.91–3.22 (5H,m), 3.41–3.70 (2H,m), 3.98–4.30 (3H,m), 6.50–6.65 (1H,m) 10 (1H,each d,J=2.2 Hz), 7.07–7.37 (8H,m), 7.57&7.65 (1H,each d,J=7.8 Hz), 8.15 (1H,broad).

Note 5) Amorphous solid
NMR (δ ppm in CDCl$_3$): 2.6–3.4 (5H,m), 3.5–3.9(3H,m), 4.0–4.5 (4H,m), 6.65 (1H,d,J=6.8 Hz), 6.71&6.75 (1H,each d,J=2.8 Hz), 6.9–7.4 (18H,m), 7.68 (1H,d,J=7.0 Hz), 8.07 (1H,broad s).

Note 6) Synthesized by catalytic reduction of N-[2-benzyl-3-(p-nitrophenyl)propionyl]-(L)-tryptophanol (Reference Example 5) followed by reaction with benzoyl chloride.

Note 7) Synthesized by catalytic reduction of N-[2-benzyl-3-(p-nitrophenyl)propionyl]-(L)-tryptophanol (Reference Example 5) followed by reaction with acetyl chloride.

Note 8) Synthesized by catalytic reduction of N-[2-benzyl-3-(p-nitrophenyl)propionyl]-(L)-tryptophanol (Reference Example 5) followed by reaction with tosyl chloride.

Note 9) Synthesized by reaction of N-(2-carboxy-3-phenylpropionyl)-(L)-tryptophanol (Reference Example 8) with dibenzylamine using the method described for Example 1.

Note 10) Synthesized by reaction of N-(2-carboxy-3-phenylpropionyl)-(L)-tryptophanol (Reference Example 8) with benzylamine using the method described for Example 1.

Example 98

To a solution of N-benzyloxycarbonyl-(L)-phenylalanyl-(L)-tryptophanol (0.60 g) and triethylamine (0.53 ml) in dimethyl sulfoxide (DMSO) (7 ml), a solution of pyridine-sulfur trioxide complex (pyridine.$SO_3$) in DMSO (7 ml) was added drop by drop. After stirring at room temperature for 1 hour, the reaction mixture was poured over ice water and extracted with ethyl ether (60 ml×3). The ethyl ether layer was washed by sequential additions of a 10% aqueous citric acid solution, a saturated aqueous sodium hydrogen carbonate solution and saturated saline and then dried ($MgSO_4$). After the solvent was distilled off, the residue was solidified from THF-hexane-ethyl ether to yield N-benzyloxycarbonyl-(L)-phenylalanyl-(L)-tryptophanal (0.44 g, 74%) as a colorless powder.

Melting point: 74–77° C. $[\alpha]_D$=+18.0° (c 0.05, $CHCl_3$, 31° C.)

Examples 99 through 117

The same procedure as in Example 98 was followed to yield the compounds listed in Table 9.

TABLE 9

| Example No. | R | Melting Point (° C.) | Recrystallization Solvent | Optical Rotation $[\alpha]_D$ (c, solvent) |
|---|---|---|---|---|
| 99 | 3-Tol—NHCO—Ile— | 202–204 (decomposed) | Methanol-dichloromethane-hexane | −20.8° (c 0.32, DMSO) |
| 100 | 1-Nap—$SO_2$— | 160–161 | Ethyl ether | −84.6° (c 0.5, $CHCl_3$) |
| 101 | 4-Tol—$SO_2$—Ile— | 199–201 | — | −32.70° (c 0.51, $CH_3OH$) |
| 102 | tBuOCO—Ile— | 114–115 | Isopropyl ether | +22.3° (c 0.775, $CHCl_3$) |
| 103 | 1-Nap—$SO_2$—Ile— | 145–146 | Ethyl acetate-hexane | −54.4° (c 0.50, $CHCl_3$) |
| 104 | $PhCH_2OCO$— | 105–106 | Ethyl acetate-isopropyl ether | −49.0° (c 0.5, $CHCl_3$) |
| 105 | 4-Tol—$SO_2$—Phe— | 150–151 | Ethyl acetate-ethyl ether | +15.4° (c 0.41, DMSO) |
| 106 | 1-Nap—$SO_2$—Gly— | 135–136 | — | −54.8° (c 0.50, $CHCl_3$) |
| 107 | $PhCH_2OCO$—Ile— | 137–140 | Ethyl acetate-hexane | +28.5° (c 0.4, MeOH) |
| 108 | $PhCH_2OCO$—Ile—Ile— | Note [1] | — | +12.5° (c 0.12, $CHCl_3$) |
| 109 | tBuOCO—Ile—Ile— | 178–180 | Tetrahydrofuran-dichloromethane-hexane | −36.5° (c 0.115, DMSO) |
| 110 | 1-Nap—$SO_2$—Ile—Ile— | 159–160 | Tetrahydrofuran-ethyl ether-hexane | −100.0° (c 0.125, $CHCl_3$) |
| 111 | $CH_3OCO(CH_2)_2$CO—Ile—Ile— | Note [2] | — | — |
| 112 | 1-Ad($CH_2)_2OCO$—Ile—Ile— | Note [3] | — | — |
| 113 | $(C_3H_7)_2CHCO$— | 135–136 | Dichloromethane-ethyl ether | −86.8° (c 0.5, $CHCl_3$) |
| 114 | Ph.$CH_2NHCO$—Ile— | 183–185 | Chloroform-ethyl acetate | −16.9° (c 0.4, DMSO) |
| 115 | ⌬—$(CH_2)_2NHCO$—Ile- | 168–169 | Dichloromethane-ethyl acetate-hexane | −21.9° (c 0.325, DMSO) |

TABLE 9-continued

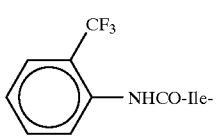

| Example No. | R | Melting Point (° C.) | Recrystallization Solvent | Optical Rotation [α]<sub>D</sub> (c, solvent) |
|---|---|---|---|---|
| 116 | (CH₃)₂CHNHCO—Ile— | 201–204 (decomp.) | Methanol-ethyl acetate | −15.9° (c 0.57, DMSO) |
| 117 | 2-CF₃-C₆H₄-NHCO-Ile- | 185–186 (decomp.) | Methanol-ethyl acetate | −18.7° (c 0.50, DMSO) |

Ile: (L)-isoleucine, Phe: (L)-phenylalanine, Gly: glycine, tBu: tert-butyl, 1-Nap: 1-naphthyl, 3-Tol: 3-tolyl, 4-Tol: 4-tolyl, Ph: phenyl, 1-Ada: adamantan-1-yl Note 1) Amorphous solid
NMR (δ ppm in CDCl₃): 0.84–0.90 (12H, m), 0.98–1.17 (2H, m), 1.36–1.51 (2H, m), 1.81–1.94 (2H, m), 3.27–3.33 (2H, m), 4.00 (1H, dd, J=6.8 & 8.6 Hz), 4.30 (1H, dd, J=6.8 & 8.6 Hz), 4.80 (1H, dd, J=6.6 & 13.2 Hz), 5.10 (2H, s), 5.28 (1H, d, J=7.6 Hz), 6.48 (1H, d, J=8.6 Hz), 6.62 (1H, d, J=6.6 Hz), 7.03–7.40, 7.55–7.60 (10 H, m), 8.25 (1H, br s), 9.63 (1H, s). SI-MS m/z: 549 (MH⁺).

Note 2) Amorphous solid
NMR (δ ppm in d₆-DMSO): 0.75–0.81 (12H, m), 0.98–1.13 (2H, m), 1.33–1.47 (2H, m), 1.66–1.75 (2H, m), 2.40–2.51 (4H, m), 2.93–3.25 (2H, m), 3.56 (3H s), 4.16–4.26 (2H, m), 4.41 (1H, dd, J=7.0 & 13.0 Hz), 6.94–7.17 (3H, m), 7.34 (1H, d, J=8.0 Hz), 7.52 (1H, d, J=7.6 Hz), 7.79 (1H, d, J=8.6 Hz), 7.96 (1H, d, J=8.8 Hz), 8.42 (1H, d, J=6.4 Hz), 9.47 (1H, s), 10.86 (1H, br s). SI-MS m/z: 529 (MH⁺).

Note 3) Amorphous solid
NMR (δ ppm in CDCl₃): 0.85–0.91 (12H, m), 1.02–1.19 (2H, m), 1.36–1.96 (21H, m), 3.20–3.41 (2H, m), 3.93–4.02 (1H, m), 4.09–4.16 (2H, m), 4.32 (1H, dd, J=6.8 & 8.4 Hz), 4.82 (1H, dd, J=7.0 & 13.4 Hz), 5.12 (1H, d, J=8.2 Hz), 6.48 (1H, d, J=8.6 Hz), 6.63 (1H, d, J=7.0 Hz), 7.03–7.25 (3H, m), 7.37 (1H, d, J=7.4 Hz), 7.59 (1H, d, J=7.2 Hz), 8.28 (1H, br s), 9.63 (1H, s) SI-MS m/z: 621 (MH⁺).

Example 118

The same procedure as in Example 98 was followed to yield N-(1naphthylsulfonyl)-(L)-isoleucyl-(L)-isoleucyl-(DL)-(1-naphthyl)alaninal, which was recrystallized from ethyl acetate-tetrahydrofuran-hexane.

Melting point: 169–174° C. NMR (δ ppm in CD₃OD): 0.2–1.7 (8H, m), 3.0–3.2 (1H, m), 3.45 (1H, dd, J=7.2 & 18.0 Hz), 3.61 (1H, dd, J=4.0 & 14.2 Hz), 3.87 (1H, dd, J=7.2 & 24.6 Hz), 4.2–4.4 (1H, m), 7.3–8.3 (13H, m), 8.74 (1H, t, J=8.6 Hz)

Example 119 through 149

The same procedure as in Example 98 was followed to yield the compounds listed in Table 10.

TABLE 10

| Example No. | R | Melting Point (° C.) | Recrystallization Solvent | Optical Rotation [α]<sub>D</sub> (c, solvent) |
|---|---|---|---|---|
| 119 | PhCH₂OCO—Gly— | 131–132 | ether-hexane | −16.1° (0.50, CH₃OH) |
| 120 | tBuOCO—Phe— | 85–86 | Ethyl acetate-hexane | +17.4° (0.71, CHCl₃) |
| 121 | 1-Nap—SO₂—Phe— | 85–86 | Ethyl acetate- | −71.5° |

TABLE 10-continued

[Structure: L-tryptophan-derived aldehyde with R—NH— group and —CHO, showing (L) stereochemistry with H below]

| Example No. | R | Melting Point (° C.) | Recrystallization Solvent | Optical Rotation [α]$_D$ (c, solvent) |
|---|---|---|---|---|
| 122 | (PhCH$_2$)$_2$CHCO— | (dec.) 142–144 | isopropyl ether Ethyl acetate-isopropyl ether | (0.745, CHCl$_3$) +14.1° (0.57, CHCl$_3$) |
| 123 | PhCH$_2$CH$_2$CO— | 124–125 | CH$_2$Cl$_2$—ether | +60.0° (0.58, CHCl$_3$) |
| 124 | 1-Nap—SO$_2$—Ala— | 119–120 (dec.) | ether | +26.7° (0.50, CH$_3$OH) |
| 125 | (C$_3$H$_7$)$_2$CHCO—Ala— | 141–142 | ether | −52.6° (0.715, CH$_3$OH) |
| 126 | PhCH$_2$OCO—Trp— | 86–88 | Ethyl acetate-isopropyl ether | −7.6 (0.715, CHCl$_3$) |
| 127 | tBuOCO—Trp— | 95–97 | ether-hexane | −23.0° (0.68, DMSO) |
| 128 | PhCO—Phe— | 113–115 (dec.) | DMF—H$_2$O | −55.9° (0.78, DMSO) |
| 129 | (PhS)(C$_3$H$_7$)CHCO— | 111–112 | CH$_2$Cl$_2$—ether | +106.6° (0.52, CHCl$_3$)) |
| 130 | PhCH$_2$NHCS—Ile— | 130–131 | Ethyl acetate-isopropyl ether | −12.9° (0.34, DMSO) |
| 131 | 1-Nap—NHCO—Ile— | 192–193 (dec.) | Ethyl acetate-hexane | +4.4° (0.395, DMSO) |
| 132 | PhCH$_2$OCO—Val— | 98–99 | ether-hexane | −34.4° (0.50, CH$_3$OH) |
| 133 | 1-Nap—SO$_2$—Val— | 117–118 | ether-hexane | −17.2° (0.50, CH$_3$OH) |
| 134 | PhCO—Val— | 120–121 | ether-hexane | −26.9° (0.50, CH$_3$OH) |
| 135 | (C$_3$H$_7$)$_2$CHCO—Val— | 149–150 | Ethyl acetate-hexane | −48.8° (0.50, CH$_3$OH) |
| 136 | (2-benzimidazolyl-S)(C$_3$H$_7$)CHCO— | 119–120 | CH$_2$Cl$_2$—ether | −28.4° (0.25, CH$_3$OH) |
| 137 | PhNHCS—Ile— | —[1] | — | +18.8° (0.485, CHCl$_3$) |
| 138 | 1-Nap—NHCS—Ile— | —[2] | — | +34.2° (0.325, CHCl$_3$) |
| 139 | PhCO—Gly | —[3] | — | −11.0° (0.50, CH$_3$OH) |
| 140 | PhCH$_2$OCO—Ala— | 120–121 | ether | +22.9° (0.50, CHCl$_3$) |
| 141 | PhCH$_2$OCO—Leu— | —[4] | — | +15.4° (0.50, CHCl$_3$) |
| 142 | 1-Nap—SO$_2$—Leu— | 81–82 | Ethyl acetate-hexane | −40.5° (0.50, CHCl$_3$) |
| 143 | PhCO—Leu— | 162–163 | Ethyl acetate-hexane | −30.4° (0.50, CH$_3$OH) |
| 144 | (C$_3$H$_7$)$_2$CHCO—Leu— | 107–108 | Ethyl acetate-hexane | +2.6° (0.50, CHCl$_3$) |
| 145 | (C$_3$H$_7$)$_2$CHCO—Gly— | 68–69 | Ethyl acetate hexane | +42.8° (0.50, CHCl$_3$) |
| 146 | PhCO—Ile— | 188–190 | Ethyl acetate-hexane | +45.4° (0.26, CHCl$_3$) |
| 147 | Ph(CH$_2$)$_3$CO— | —[5] | — | −17.4° (0.665, CHCl$_3$) |
| 148 | (C$_3$H$_7$)$_2$CHCO—Phe— | 141–142 | Ethyl acetate-hexane | −19.1° (0.50, CH$_3$OH) |
| 149 | (C$_3$H$_7$)$_2$CHCO—Ile— | 143–144 | Ethyl acetate-hexae | −41.7° (0.50, CH$_3$OH) |

DMSO: dimethyl sulfoxide, DMF: N,N-dimethylformamide, Ph: phenyl, 1-Nap: 1-naphtyl, tBu: tert.butyl, Ile:(L)-isoleucine, Leu:(L)-leucine, Ala:(L)-alanine, Gly: glycine, Val: (L)-valine, Trp: (L)-tryptophan, Phe: (L)-phenylalanine, Note 1) Amorphous solid NMR (δ ppm in CDCl₃): 0.8–1.2 (7H,m), 1.3–1.5 (1H,m), 1.8–2.0 (1H,m), 3.23 (1H,dd,J=6.6&15.0 Hz), 3.34 (1H,dd, J=6.0&15.0 Hz), 4.77 (1H,q,J=6.6&13.0 Hz), 4.91 (1H,t,J= 8.0 Hz), 6.65 (1H,d,J=6.6 Hz), 6.73 (1H,d,J=8.4 Hz), 7.0–7.4 (9H,m), 7.57 (1H,d,J=8.4 Hz), 8.18 (1H,broad s), 9.60 (1H,s).

Note 2) Amorphous solid

NMR (δ ppm in CDCl₃): 0.6–1.3 (8H,m), 1.7–1.9 (1H,m), 3.26 (2H,dd,J=4.8&6.4 Hz), 4.70 (1H,q,J=6.6&13.0 Hz), 4.88 (1H,t,J=8.4 Hz), 6.23 (1H,d,J=8.4 Hz),6.62 (1H,d,J=7.0 Hz), 7.1–8.3 (14H,m),9.58 (1H,s).

Note 3) Amorphous solid

NMR (δ ppm in CDCl₃): 3.30 (2H,dJ=7.0 Hz), 4.07 (2H,d,J=5.0 Hz), 4.76 (1H,q,J=7.0 Hz), 6.98 (1H,d,J=2.0 Hz), 7.01 (1H,s), 7.07 (1H,dt,J=1.0&8.0 Hz), 7.17 (1H,dt, J=1.0&8.0 Hz), 7.30 (1H,t,J=7.0 Hz), 7.41 (1H,t,J=7.0 Hz), 7.43 (1H,d,J=7.0 Hz), 7.45 (2H,d,J=8.0 Hz), 7.54 (1H,d,J= 7.0 Hz), 7.73 (2H,d,J=8.0 Hz), 8.28 (1H,s), 9.61 (1H,s).

Note 4) Amorphous solid

NMR (δ ppm in CDCl₃): 0.89 (6H,d,J=6.0 Hz), 1.45–1.50 (1H,m), 1.56–1.66 (2H,m), 3.28 (2H,t,J=7.0 Hz), 4.18–4.28 (1H,m), 4.74 (1H,q,J=6.0 Hz), 5.04 (2H,s), 5.12 (1H,d,J=9.0 Hz), 6.68 (1H,d,J=6.0 Hz), 6.95 (1H,s), 7.11 (1H,dt,J= 1.0&7.0 Hz), 7.19 (1H,dt,J=1.0&7.0 Hz), 7.31 (1H,d,J= 1.0Hz), 7.34 (5H,s), 7.57 (1H,d,J=8.0 Hz), 8.08 (1H,s), 9.60 (1H,s).

Note 5) Amorphous solid

NMR (δ ppm in CDCl₃): 1.93 (2H,quintet,J=7.6 Hz), 2.18 (2H,t,J=7.6 Hz), 2.61 (2H,t,J=7.6 Hz), 3.24 (1H,dd,J= 15.0&7.0 Hz), 3.38 (1H,dd,J=15.0&5.4 Hz),4.83 (1H,m), 6.03 (1H,d,J=4.0 Hz), 6.90–7.30 (8H,m), 7.60 (1H,d,J=7.8 Hz), 8.19 (1H,broad s), 9.62 (1H,s).

Examples 150 through 164

The same procedure as in Example 98 was followed to yield the compounds listed in Table 11.

TABLE 11

| Example No. | R⁴ | R¹ | Melting Point (° C.) | Recrystallization Solvent | Optical Rotation [α]_D (c, solvent) |
|---|---|---|---|---|---|
| 150 | tBuOCO— | —CH₂—(1-methylindol-3-yl) | 107–108 | Ethyl acetate-hexane | −25.7° (0.49, DMSO) |
| 151 | PhCH₂OCO— | —CH₃ | 164–165 | Ethyl acetate | −26.7° (0.305, DMSO) |
| 152 | PhCH₂OCO— | —CH₂Ph | 138–139 | Ethyl acetate-hexane | −47.4° (0.34, DMSO) |
| 153 | 1-Nap—SO₂— | —CH₃ | 150–151 | Ethyl acetate-hexane | +36.7° (0.45, DMSO) |
| 154 | 1-Nap—SO₂— | —CH₂Ph | 138–139 | Ethyl acetate-hexane | −24.3° (0.595, DMSO) |
| 155 | PhCH₂OCO— | —CH₂—(1-tert-butylindol-3-yl) | 81–82 | Ethyl acetate-hexane | +27.7° (0.33, CHCl₃) |
| 156 | PhCH₂OCO— | —CH₂—C₆H₄—OH (p) | 103–104 | Ethyl acetate-hexane | −40.0° (0.37, DMSO) |
| 157 | PhCH₂OCO— | —CH₂—C₆H₄—OCH(CH₃)₂ (p) | 155–156 | Ethyl acetate-hexane | −44.6° (0.315, DMSO) |

TABLE 11-continued $$R^4-NH-\overset{(L)}{\underset{H}{C}}-CONH-\overset{(L)}{\underset{H}{C}}-CHO$$

(with isobutyl-like group on left carbon and $R^1$ on right carbon)

| Example No. | $R^4$ | $R^1$ | Melting Point (° C.) | Recrystallization Solvent | Optical Rotation $[\alpha]_D$ (c, solvent) |
|---|---|---|---|---|---|
| 158 | 1-Nap—SO$_2$— | —CH$_2$—C$_6$H$_4$—OH | —[1] | — | −20.4° (0.305, CHCl$_3$) |
| 159 | 1-Nap—SO$_2$— | —CH$_2$—C$_6$H$_4$—OCH(CH$_3$)$_2$ | 117–118 | Ethyl acetate-hexane | −16.4° (0.45, DMSO) |
| 160 | PhCH$_2$OCO— | —CH(CH$_3$)$_2$ | 122–123 | Ethyl acetate-hexane | +4.2° (0.29, DMSO) |
| 161 | PhCH$_2$OCO— | —CH$_2$CH(CH$_3$)$_2$ | 157–158 | Ethyl acetate-hexane | −29.5° (0.35, DMSO) |
| 162 | 1-NapSO$_2$— | —CH(CH$_3$)$_2$ | 145–146 | Ethyl acetate-hexane | +24.3° (0.515, DMSO) |
| 163 | 1-NapSO$_2$— | —CH$_2$CH(CH$_3$)$_2$ | 155–156 | Ethyl acetate-hexane | +12.9° (0.82, DMSO) |
| 164 | PhCH$_2$OCO— | H | 169–171 | Ethyl acetate-hexane | −10.5° (0.50, CHCl$_3$) |

DMSO: dimethyl sulfoxide, Ph: phenyl, 1-Nap: 1-naphthyl, tBu: tert.butyl,

Note 1) Amorphous solid
NMR (δ ppm in CDCl$_3$): 0.4–0.7 (6H,m), 0.7–1.0 (1H,m), 1.0–1.2 (1H,m), 1.5–1.8 (1H,m), 2.58 (1H,dd,J=7.0&14.0 Hz), 2.74 (1H,dd,J=6.6&14.0 Hz), 3.59 (1H,dd,J=5.6&7.8 Hz), 4.38 (1H,q,J=6.6&13.6 Hz), 5.81 (1H,d,J=8.0 Hz), 6.5–7.0 (6H,m), 7.4–7.7 (3H,m), 7.91 (1H,d,J=8.0 Hz), 8.05 (1H,d,J=8.0 Hz), 8.23 (1H,d,J=7.4 Hz), 8.68 (1H,d,J=8.0 Hz), 9.16 (1H,s).

Examples 165 through 169

The same procedure as in Example 98 was followed to yield the compounds listed in Table 12.

TABLE 12

$$R-NH-\overset{(L)}{\underset{H}{C}}-CHO$$

| Example No. | R | $R^1$ | Melting Point (° C.) | Recrystallization Solvent | Optical Rotation $[\alpha]_D$ (c, solvent) |
|---|---|---|---|---|---|
| 165 | (PhCH$_2$)$_2$CHCO— | —CH$_2$Ph | 113–114 | CH$_2$Cl$_2$—isopropyl ether | +29.0° (0.59, CHCl$_3$) |
| 166 | PhCH$_2$OCO—Leu—Leu— | H | 110–111 | Ethyl acetate-hexane | −51.2° (0.50, CH$_3$OH) |
| 167 | (PhCH$_2$)$_2$CHCO— | —CH$_2$CH$_3$ | 141–142 | CH$_2$Cl$_2$—hexane | +19.3° (0.51, CHCl$_3$) |
| 168 | (PhCH$_2$)$_2$CHCO— | —CH(CH$_3$)$_2$ | 139–140 | CH$_2$Cl$_2$—hexane | +40.4° (0.53, CHCl$_3$) |
| 169 | (PhCH$_2$)$_2$CHCO— | —CH$_3$ | 136–137 | CH$_2$Cl$_2$—hexane | −3.9° (0.55, CHCl$_3$) |

Leu: (L)-leucine, Ph: phenyl

Example 170

The same procedure as in Example 98 was followed to yield N-benzyloxycarbonyl-(L)-isoleucyl-(D)-tryptophanal and recrystallized from ethyl acetate-hexane. Melting point 163–164° C. $[\alpha]_D$=+37.2° (c0.635, DMSO)

Example 171

The same procedure as in Example 98 was followed to yield N-(1-naphthylsulfonyl)-(L)-isoleucyl-(D)-tryptophanal as an amorphous solid. $[\alpha]_D$=−39.3° (c0.30, CHCl$_3$)

NMR(δ ppm in CDCl$_3$): 0.50 (3H,d,J=6.8 Hz), 0.62 (3H,t,J=7.6 Hz), 0.7–0.9 (1H,m), 1.2–1.4 (1H,m), 1.5–1.8 (1H,m), 2.90 (1H,dd,J=7.4&14.8 Hz), 3.12 (1H,dd,J= 8.0&14.8 Hz), 3.53 (1H,dd,J=5 .4&7.8 Hz), 4.36 (1H,dd,J= 6.2&13.0 Hz), 5.47 (1H,d,J=8.0 Hz), 6.50 (1H,d,J=6.6 Hz), 7.0–8.3 (12H,m), 8.63 (1H,d,J=8.4 Hz), 9.19 (1H,s).

Examples 172 through 193

The same procedure as in Example 98 was followed to yield the compounds listed in Table 13 and 14.

TABLE 13

R—NH—*C(L)(H)—CHO with R¹ substituent

| Example No | R | R¹ | Melting Point (° C.) | Recrystallization Solvent | Optical Rotation $[\alpha]_D$ (c, solvent) |
|---|---|---|---|---|---|
| 172 | (C$_3$H$_7$)$_2$CHCO— | PhCH$_2$— | 108–109 | CH$_2$Cl$_2$-ether-isopropyl ether | +88.9° (0.5, CHCl$_3$) |
| 173 | Ph(CH$_2$)$_3$CO— | PhCH$_2$— | 112–113 | AcOEt-ether-hexane | +53.7° (0.535, CHCl$_3$) |
| 174 | PhCH$_2$OCO—Leu— | H | 93–94 | AcOEt-hexane | +2.6° (0.23, CHCl$_3$) |
| 175 | 1-Nap—SO$_2$—Leu—Trp— | H | 177–178 | AcOEt | −13.1° (0.235, DMSO) |

Leu: (L)-leucine, Trp: (L)-tryptophan, Ph: phenyl, 1-Nap: 1-naphthyl, AcOEt: ethyl acetate

TABLE 14

R—NH—*C(L)(H)—CHO with indol-3-ylmethyl substituent

| Example No. | R | Melting Point (° C.) | Recrystallization Solvent | Optical Rotation $[\alpha]_D$ (c, solvent) |
|---|---|---|---|---|
| 176 | (CH$_3$)$_2$CHCH$_2$CH$_2$CO— | 50–51 | AcOEt-hexane | −34.1° (0.5, CH$_3$OH) |
| 177 | cyclohexyl-CO— | 138–139 | AcOEt-hexane | −41.5° (0.5, CH$_3$OH) |
| 178 | Ph—CO— | 134–135 | AcOEt-hexane | −97.2° (0.5, CH$_3$OH) |
| 179 | Ph(C$_2$H$_5$)CH—CO— | —[1] | AcOEt-hexane | +12.6 (0.585, CHCl$_3$) |
| 180 | (PhCH$_2$)[(4-CH$_3$—C$_6$H$_4$)CH$_2$]CH—CO— | —[2] |  | +32.3° (0.475, CHCl$_3$) |
| 181 | PhCH$_2$CH$_2$—CO—Val— | 161–162 | AcOEt-hexane | −72.1° (0.50, CH$_3$OH) |
| 182 | (PhCH$_2$)$_2$CH—CO—Val— | 156–157 | AcOEt-hexane | −44.0° (0.50, CH$_3$OH) |
| 183 | (PhCH$_2$)[(2-CH$_3$O—C$_6$H$_4$)CH$_2$]CH—CO— | 136–138 | AcOEt-hexane | +15.5° (0.475, CHCl$_3$) |
| 184 | (PhCH$_2$)[(4-CH$_3$O—C$_6$H$_4$)CH$_2$]CH—CO— | —[3] |  | +15.7° (0.54, CHCl$_3$) |
| 185 | [(4-PhCONH—C$_6$H$_4$)—CH$_2$](PhCH$_2$)CH—CO— | 190–191 | AcOEt-hexane | −69.9° (0.405, CHCl$_3$) |
| 186 | [(4-CH$_3$CONH—C$_6$H$_4$)—CH$_2$](PhCH$_2$)CH—CO— | 124–125 | AcOEt-hexane | −32.4° (0.225, DMSO) |
| 187 | [(4-Tol—SO$_2$NH—C$_6$H$_4$)—CH$_2$](PhCH$_2$)CH—CO— | —[4] |  | +22.2° (0.415, CHCl$_3$) |
| 188 | [[4-(C$_2$H$_5$O)$_2$P(O)— |  |  | −5.8° |

TABLE 14-continued

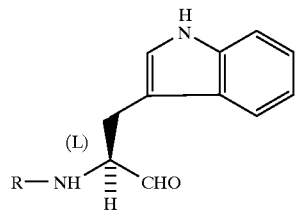

| Example No. | R | Melting Point (° C.) | Recrystallization Solvent | Optical Rotation [α]_D (c, solvent) |
|---|---|---|---|---|
|  | CH₂]C₆H₄NHCO](Ph—CH₂)CH—CO— |  |  | (0.665, CHCl₃) |
| 189 | (C₂H₅OOC)(PhCH₂)CH—CO— | —6) |  | +22.3° (0.66, CHCl₃) |
| 190 | [(PhCH₂)₂N—CO](PhCH₂)₂CHCO— | —7) |  | +6.6° (0.90, CHCl₃) |
| 191 | (PhCH₂NH—CO)(PhCH₂)CHCO— | —8) |  | −14.2° (0.94, DMSO) |
| 192 | Ph₂CH—CO— | 172–173 | AcOEt-hexane | −8.0° (0.37, DMSO) |
| 193 | (4-oxo-4H-1-benzopyran-2-yl)-CO—Ile— | 120–121 | AcOEt-hexane | −69.8° (0.50, CH₃OH) |

Leu: (L)-leucine, Val: (L)-valine, Ph: phenyl, Tol: 4-tolyl, AcOEt: ethyl acetate Note 1) Amorphous solid
NMR (δ ppm in CDCl₃): 0.86 (3H,t,J=7.4 Hz), 1.80 (1H,m), 2.17 (1H,m), 3.13–3.37 (3H,m), 4.64 (1H,q,J=6.6 Hz), 6.06 (1H,d,J=5.8 Hz), 6.75 (1H,d,J=2.0 Hz), 7.00–7.40 (7H,m), 7.55 (1H,d,J=7.8 Hz), 8.07 (1H,broad s), 9.53 (1H,s).

Note 2) Amorphous solid
NMR (δ ppm in CDCl₃): 2.27&2.30 (3H,each s), 2.46–2.66 (1H,m), 2.72–3.24 (6H,m), 5.53–5.70 (1H,m), 6.37–6.52 (1H,m), 6.88–7.50 (13H,m), 7.95 (1H,broad), 9.19&9.21 (1H,each s).

Note 3) Amorphous solid
NMR (δ ppm in CDCl₃): 2.35–3.20 (7H,m), 3.75&3.77 (3H,each s), 4.42–4.58 (1H,m), 5.50–5.62 (1H,m), 6.32&6.38 (1H,each d,J=2.4 Hz), 6.72–6.88 (2H,m), 7.00–7.60 (11H,m), 7.92 (1H,broad s), 9.19&9.25 (1H,each broad s).

Note 4) Amorphous solid
NMR (δ ppm in CDCl₃): 2.30 (3H,s), 2.5–3.1 (7H,m), 4.2–4.4 (1H,m), 5.72 (1H,d,J=6.6 Hz), 6.25 (1H,d,J=1.8 Hz), 6.8–7.4 (15H,m), 7.59 (2H,d,J=8.2 Hz) 8.32 (1H,broad s), 9.13 (1H,s).

Note 5) Amorphous solid
NMR (δ ppm in CDCl₃): 1.21 (3H,t,J=7.0 Hz), 1.22 (3H,t,J=7.0 Hz), 3.0–3.3 (6H,m), 3.5–3.7 (1H,m), 3.8–4.1 (4H,m), 4.5–4.7 (1H,m), 6.65&6.71 (1H,each d,J=1.6 Hz), 7.0–7.6 (13H,m), 8.44&8.61 (1H,each broad s), 9.27&9.39 (1H,each broad s), 9.42&9.47 (1H,each s).

Note 6) Oil
NMR (δ ppm in CDCl₃): 1.12 (3H,t,J=6.2 Hz), 3.1–3.6 (5H,m), 4.02 (2H,q,J=14.2&6.2 Hz), 4.6–4.8 (1H,m), 6.81&6.92 (1H,each d,J=2.2 Hz), 7.0–7.4 (9H,m), 7.49&7.59 (1H,each d,J=7.4 Hz), 8.22 (1H,broad s), 9.51&9.54 (1H,each s).

Note 7) Amorphous solid
NMR (δ ppm in CDCl₃): 3.0–3.4 (4H,m), 3.85 (1H,dt,J=10.4&4.2 Hz), 4.0–4.5 (4H,m), 4.6–4.8 (1H,m), 6.6–6.8 (2H,m), 6.9–7.3 (17H,m), 7.4–7.7 (2H,m), 8.33&8.38 (1H, each s), 9.56(1H,s).

Note 8) Amorphous solid
NMR (δ ppm in CDCl₃): 2.9–3.3 (4H,m), 3.54 (1H,t,J=7.2 Hz), 4.0–4.5 (3H,m), 6.9–7.5 (15H,m), 8.23 (1H,d,J=7.0 Hz), 8.29 (1H,t,J=7.0 Hz), 9.43&9.47 (1H,each s), 10.86 (1H,s).

Example 194

To a solution of N-(1-naphthylsulfonyl)-(L)-isoleucyl-(L)-tryptophanol (1.0 g) and acetyl chloride (0.171 g) in N,N-dimethylformamide (6 ml) was added 4-(N,N-dimethylamino)pyridine (0.28 g) under ice-cooling and stirred for 3 hours at the same temperature. The reaction mixture was poured on ice-water and extracted with ethyl acetate. The ethyl acetate layer was washed sequentially with an aqueous citric acid solution, water, an aqueous sodium bicarbonate solution and water, and dried (MgSO₄). After the solvent was distilled off, the residue was subjected to silica gel column chromatography. O-acetyl compound of N-(1-naphthylsulfonyl)-(L)-isoleucyl-(L)-tryptophanol (shown as Example No. 194 in Table 16) was obtained as an amorphous solid (0.83 g, 76%) from the eluted fraction of ethyl acetate-hexane (2:3, v/v).

NMR (δ ppm in CDCl₃): 0.5–0.9 (7H,m), 1.0–1.2 (1H,m), 1.6–1.8 (1H,m), 2.01 (3X,s), 2.53 (1H,dd,J=14.8&6.2 Hz), 2.63 (1H,dd,J=14.8&7.0 Hz), 3.52 (1H,dd,J=8.2&5.2 Hz), 3.68 (1H,dd,J=11.4&6.4 Hz), 3.79 (1H,dd,J=11.4&6.6 Hz), 4.1–4.3 (1H,m), 5.55 (1H,d,J=8.2 Hz), 6.10 (1H,d,J=8.4 Hz), 6.91 (1H,d,J=2.2 Hz), 7.0–7.7 (7H,m), 7.89 (1H,d,J=8.4 Hz), 8.02 (1H,d,J=8.2 Hz), 8.22 (1H,dd,J=7.2&1.2Hz), 8.29 (1H,broad s), 8.67 (1H,d,J=8.4 Hz). [α]D−31.4°(c 0.39, CHCl₃).

Elemental analysis (for C₂₉H₃₃N₃O₅S.1/2H₂O) Calcd.: C, 63.95; H, 6.29; N, 7.71 Found: C, 64.17; H, 6.20; N, 7.55

Example 195 through 198

The same procedure as in Example 194 was followed to yield the compounds listed in Table 15.

TABLE 15

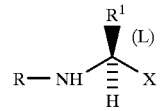

| Example No | R | R¹ | X | Melting Point (° C.) | Recrystallization Solvent | Optical Rotation [α]$_D$ (c, solvent) |
|---|---|---|---|---|---|---|
| 194 | 1-Nap—SO$_2$—Ile— | 3-Ind-CH$_2$— | —CH$_2$OCO—CH$_3$ | — | | −31.3° (0.39, CHCl$_3$) |
| 195 | 1-Nap—SO$_2$—Ile— | 3-Ind-CH$_2$— | —CH$_2$OCO—CH$_2$CH$_3$ | —[1] | | −27.8° (0.52, CHCl$_3$) |
| 196 | 1-Nap—SO$_2$—Ile— | 3-Ind-CH$_2$— | —CH$_2$OCO—Ph | —[2] | | −11.3° (0.435, CHCl$_3$) |
| 197 | (PhCH$_2$)$_2$CHCO— | 3-Ind-CH$_2$— | —CH$_2$OCO—CH$_3$ | 129–130 | AcOEt-hexane | −7.2° (0.75, DMSO) |
| 198 | 1-Nap—SO$_2$—Leu—Trp— | CH$_3$— | —CH$_2$OCO—CH$_3$ | 157–158 | AcOEt-hexane | +55.9° (0.705, DMSO) |

1-Nap: 1-naphthyl, Ile: (L)-isoleucine, Trp: (L)-tryptophan Ph: phenyl, 3-Ind: 3-indolyl, AcOEt: ethyl acetate Note 1) Amorphous solid
NMR (δ ppm in CDCl$_3$): 0.5–0.9 (7H,m), 1.00 (3H,t,J=7.6 Hz), 1.0–1.2 (1H,m), 1.5–1.8 (1H,m), 2.28 (2H,q,J=7.6 Hz), 2.51 (1H,dd,J=14.6&6.2 Hz), 2.61 (1H,dd,J=14.6&7.2 Hz), 3.53 (1H,dd,J=8.0&5.4 Hz), 3.68 (1H,dd,J=11.4&6.2 Hz), 3.79 (1H,dd,J=11.4&4.8 Hz), 4.1–4.3 (1H,m), 5.64 (1H,d,J=8.0 Hz), 6.14 (1H,d,J=8.4 Hz), 6.90 (1H,d,J=2.0 Hz), 7.0–7.7 (7H,m), 7.88 (1H,d,J=7.8 Hz), 8.01 (1H,d,J=8.2 Hz), 8.21 (1H,d,J=7.2 Hz), 8.38 (1H,broad s), 8.67 (1H,d,J=8.4 Hz).

Note 2) Amorphous solid
NMR (δ ppm in CDCl$_3$): 0.50 (3H,t,J=7.2 Hz), 0.59 (3H,d,J=6.8 Hz), 0.6–0.9 (1H,m), 1.0–1.2 (1H,m), 1.5–1.8 (1H,m), 2.53 (1H,dd,J=14.6&6.2 Hz), 2.64 (1H,dd,J=14.6&7.2 Hz), 3.57 (1H,dd,J=8.4&5.4 Hz), 3.87 (1H,dd,J=11.4&6.8 Hz), 3.97 (1H,dd,J=11.4&4.6 Hz), 4.2–4.4 (1H,m), 5.70 (1H,d,J=8.4 Hz), 6.19 (1H,d,J=8.4 Hz), 6.91 (1H,d,J=2.4 Hz), 7.0–7.6 (10H,m), 7.8–8.0 (4H,m), 8.17 (1H,dd,J=7.4&1.0 Hz), 8.40 (1H,broad s), 8.67 (1H,d,J=8.6 Hz).

| Sequence table | |
|---|---|
| SEQ ID NO: | 1 |
| Sequence length: | 20 |
| Sequence type: | Nucleic acid |
| Strandedness: | Single |
| Topology: | Linear |
| Molecule type: | Other nucleic acid (chemically synthesized DNA) |
| Antisense: | No |
| Sequence: | |
| TTTTCAGGGGGCAGTAAGAT | |
| SEQ ID NO: | 2 |
| Sequence length: | 28 |
| Sequence type: | Nucleic acid |
| Strandedness: | Single |
| Topology: | Linear |
| Molecule type: | Other nucleic acid (chemically synthesized DNA) |
| Antisense: | No |
| Sequence: | |
| CCGGATCCGGCTTTTTAGGATTGGTCTA | |
| SEQ ID NO: | 3 |
| Sequence length: | 20 |
| Sequence type: | Nucleic acid |
| Strandedness: | Single |
| Topology: | Linear |
| Molecule type: | Other nucleic acid (chemically synthesized DNA) |
| Antisense: | Yes |
| Sequence: | |
| GGGGGCTGGTAGACTGAAGA | |

-continued

| Sequence table | |
|---|---|
| SEQ ID NO: | 4 |
| Sequence length: | 28 |
| Sequence type: | Nucleic acid |
| Strandedness: | Single |
| Topology: | Linear |
| Molecule type: | Other nucleic acid (chemically synthesized DNA) |
| Antisense: | Yes |
| Sequence: | |
| CCGGATCCATTCCTCCCATGCATGCGCC | |
| SEQ ID NO: | 5 |
| Sequence length: | 12 |
| Sequence type: | Nucleic acid |
| Strandedness: | Single |
| Topology: | Linear |
| Molecule type: | Other nucleic acid (chemically synthesized DNA) |
| Antisense: | No |
| Sequence: | |
| CCCGGATCCGGG | |

What is claimed is:

1. A method for preventing or treating osteoporosis in a mammal, which comprises administering to said mammal an effective amount of a compound of the formula:

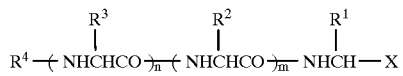

wherein $R^1$ is a hydrogen atom or (A) an arylalkyl resulting from binding of an aromatic hydrocarbon ring residue having 6 to 14 carbon atoms and a lower alkylene having 1 to 4 carbon atoms, (B) heterocyclic-alkyl resulting from binding of an aromatic heterocylic ring residue and a lower alkyl group having 1 to 4 carbon atoms, in which the aromatic heterocyclic ring is selected from the group consisting of 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol-4-yl, tetrazol-5-yl, benzimidazol-2-yl, indol-3yl, 1H-indazolyl, benz[b]furanyl, isobenzofuranyl, benz[b]thienyl, 1H-pyrrolo[2,3-b]pyradin-2-yl, 1H-pyrrolo[2,3-b]pyridin-6-yl, 1H-imidazo [4,5-p]

pyridin-2-yl, 1H-imidazol[4,5-c]pyridin-2yl and 1H-imidazo[4,5-b]pyrazin-2-yl or (C) linear or branched $C_{1-6}$ alkyl group which may be 1 to 3 substituents, at any position, selected from the group consisting of (i) linear or branched aliphatic hydrocarbon groups selected from the group consisting of $Cl_{1-10}$ alkyl groups, $C_{2-10}$ alkenyl groups and $C_{2-6}$ alkynyl groups, (ii) saturated or unsaturated alicyclic hydrocarbon groups selected from the group consisting of cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decy, 2-cyclopenten-1-yl, 3-cyclopenten-1-yl, 2-cyclohexen-1-yl, 3-cyclohexen-1-yl, 2,4-cyclopentadien-1-yl, 2,4cyclohexadien-1-yl and 2,5-cyclohexadien-1-yl, (iii) aryl group selected from the group consisting of phenyl, naphthyl, anthryl, phenanthryl, acenaphthylenyl, (iv) aromatic monocyclic heterocyclic groups selected from the group consisting of furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups selected from the group consisting of benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1.5-a]pyridyl, imidazo[1,2-a]pyridyl, imidazo[1,5-a]pyridyl, imidazo[1,2-b]pyridizinyl, imidazo[1,2-a]pyrimidinyl, 1,2,4-triazolo[4,3-a]pyridyl and 1,2,4-triazolo[4,3-b]pyridazinyl, (v) halogens selected from the group consisting of fluorine, chlorine, bromine and iodine, (vi) a nitro group, (vii) optionally substituted amino groups selected from the group consisting of amino, methylamino, dimethylamino, ethylamino, diethylamino, dibutylamino, diallylamino, cyclohexylamino, phenylamnino, N-methyl-N-phenylamino, acetylamino, propionylamino and benzoylamino, (viii) acyl groups selected from the group consisting of formyl, acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, (ix) a hydroxyl group, $C_{1-10}$ alkoxy groups, $C_{1-10}$ alkenyloxy groups, phenyl-$C_{1-4}$ alkyloxy groups, $C_{2-4}$ alkanoyloxy groups and aryloxy groups selected from the group consisting of phenoxy and 4-chlorophenoxy, (x) a thiol group, $C_{1-10}$ alkylthio groups, phenyl-$C_{1-4}$ alkylthio groups and $C_{2-4}$ alkanoylthio groups, and (xi) optionally esterified carboxyl groups selected from the group consisting of carboxy, those resulting from binding of a carboxyl group and a $C_{1-6}$ alkyl group, those resulting from binding of a carboxyl group and a $C_{3-6}$ alkenyl group, benzyloxycarbonyl and phenetyloxycarbonyl;

$R^2$ and $R^3$ independently are a hydrogen atom or (A) an arylalkyl group resulting from binding of an aromatic hydrocarbon ring residue having 6 to 14 carbon atoms and a lower $C_{1-4}$ alkylene group which may have 1 to 3 substiuents selected from the group consisting of (i) linear or branched aliphatic hydrocarbon groups selected from the group consisting of $C_{1-10}$ alkyl groups, $C_{2-10}$ alkenyl groups and $C_{2-6}$ alkynyl groups, (ii) saturated or unsaturated alicyclic hydrocarbon groups selected from the group consisting of cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl, 2-cyclopenten-1-yl, 3-cyclopenten-1-yl, 2-cyclohexen-1-yl, 3-cyclohexen-1-yl, 2,4-cyclopentadien-1-yl, 2,4-cyclohexadien-1-yl and 2,5-cyclohexadien-1-yl, (iii) aryl groups selected from the group consisting of phenyl, naphthyl, anthryl, phenanthryl, acenaphthylenyl, (iv) aromatic monocyclic heterocyclic groups selected from the group consisting of furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3, 4thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups selected from the group consisting of benzofuranyl, isobenzofuranyl, benzo[b]thienyl, indolyl, isoindolyl, 1H-indazolyl, benzimidazolyl, benzoxazolyl, 1,2-benzisoxazolyl, benzothiazoly, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]-pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl, (v) halogens selected from the group consisting of fluorine, chlorine, bromine and iodine, (VI) a nitro group, (vii) optionally substituted amino groups selected from the group consisting of amino, methylamino, dimethylamino, ethylamino, diethylamino, dibutylamino, diallylamino, cyclohexylamnino, phenylamino, N-methyl-N-phenylamino, acetylamino, propionylamino and benzoylamino, (viii) acyl groups selected from the group consisting of formyl, acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, (ix) a hydroxyl group, $C_{1-10}$ alkoxy groups, $C_{1-10}$ alkenyloxy groups, phenyl-$C_{1-4}$ amyloxy groups, $C_{2-4}$ alkanoyloxy groups and aryloxy groups selcted from the group consisting of phenoxy and 4-chlorophenoxy, (x) a thiol group, $C_{1-10}$ alkylthio groups, phenyl-$C_{1-4}$ alkylthio groups and $C_{2-4}$ alkanoylthio groups, and (xi) optionally esterified carboxyl groups selected from the group consisting of carboxy, those resulting from binding of a carboxyl group and a $C_{1-6}$ alkyl group, those resulting from binding of carboxyl group and a $C_{3-6}$ alkenyl group, benzyloxycarbonyl and phenetyloxycarbonyl or (B) a hydrocarbon group selected from the group consisting of linear or branched saturated aliphatic hydrocarbon residues having 1 to 8 carbon atoms, unsaturated aliphatic hydrocarbon residues having 2 to 8 carbon atoms, saturated alicyclic hydrocarbon residues having 3 to 7 carbon atoms, unsaturated alicyclic hydrocarbon residues having 5 to 7 carbon atoms and groups resulting from binding of (a) a saturated alicyclic hydrocarbon residue having 3 to 7 carbon atoms or an unsaturated alicyclic hydrocarbon residue having 5 to 7 carbon atoms and (b) a saturated aliphatic hydrocarbon residue having 4 to 9 carbon atoms, which hydrocarbon group may have 1 to 3 substituents selected from the group consisting of (i) halogens selected from the group consisting of fluorine, chlorine, bromine and iodine, (ii) nitro, (iii) optionally substituted amino groups selected from the group consisting of amino, methylamino, dimethylamino, ethylamino, diethylamino, dibutylamino, diallylamino, cyclohexylamino, phenylamino, N-methyl-N-phenylamino, acetylamino, propionylamino and benzoylamino, (iv) acyl groups selected from the group consisting of formyl, acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, (v) a hydroxyl group, $C_{1-10}$ alkoxy groups, $C_{1-10}$ alkenyloxy groups, phenyl-$C_{1-4}$ alkyloxy groups, $C_{2-4}$ alkanoyloxy groups and aryloxy groups selected from the group consisting of phenoxy and 4-chlorophenoxy, (vi) a thiol group, $C_{1-10}$ alkylthio groups, phenyl-$C_{1-4}$ alkylthio groups and $C_{2-4}$ alkanoylthio groups, and (vii) optionally esterified carboxyl groups selected from the group consisting of carboxy, those resulting from binding of a carboxyl group and a $C_{1-6}$ alkyl group, those resulting from binding of a carboxyl group and a $C_{3-6}$ alkenyl group, benzyloxycarbonyl and phenetyloxycarbonyl;

$R^4$ is:

(1) a $C_{2-6}$ alkanoyl group substituted by $C_{9-12}$ aryl, or (2) a sulfonyl group, a carbamoyl group or a thiocarbamoyl group, each of said groups being substituted by (i) aryl having more than 9 carbon atoms selected from the group consisting of naphthyl, anthryl, phenanthryl and acenaphthylenyl, or (ii) $C_{1-6}$ alkyl; X is formula —CHO or —CH$_2$OB (wherein B is a hydrogen atom or a protacting group of hydroxy group); m and n independently are an integer of 0 or 1; or a salt thereof.

2. The method according to claim 1 wherein $R^1$ is an indolyl-lower ($C_{1-4}$) alkyl.

3. The method according to method according to claim 1 wherein $R^1$ is a naphthyl-lower ($C_{1-4}$) alkyl.

4. The method according to claim 1 wherein $R^1$ is a phenyl-lower ($C_{1-4}$) alkyl.

5. The method according to claim 1 wherein $R^1$ is a hydrogen or lower ($C_{1-6}$) alkyl.

6. The method according to claim 1 wherein $R^2$ is a branched lower ($C_{1-10}$) alkyl.

7. The method according to claim 1 wherein $R^2$ is a phenyl-lower ($C_{1-4}$) alkyl.

8. The method according to claim 1 wherein $R^3$ is a branched lower ($C_{1-10}$)alkyl.

9. The method according to claim 1 wherein $R^3$ is a hydrogen.

10. The method according to claim 1 wherein X is —CH or —CH$_2$OH.

11. The method according to claim 1 wherein m is 1 and n is 1.

12. The method according to claim 1 wherein m is 1 and n is 0.

13. The method according to claim 1 wherein m is 0 and n is 0.

14. The method according to claim 1 wherein $R^1$ is a lower ($C_{1-6}$) alkyl which may be substituted by indolyl; $R^2$ is a lower ($C_{1-10}$) alkyl; $R^4$ is a naphthylsulfonyl or dibenzylacetyl; X is —CHO or —CH$_2$OH; m is 0 or 1 and n is 0.

15. The method according to claim 1, which contains N-dibenzylacetyl-(L)-tryptophanal.

16. The method according to claim 1, which contains N-(1-naphthylsulfonyl)-(L)-isoleucyl-(L)-alaninal.

17. The method according to claim 1, which contains N-(1-naphthylsulfonyl)-(L)-isoleucyl-(L)-tryptophanal.

18. A method for inhibiting bone resorption in a mammal, comprising administering to said mainmal an effective bone resorption inhibiting amount of a compound of the formula:

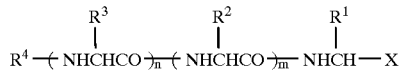

wherein $R^1$ is a hydrogen atom or (A) an arylakyl resulting from binding of an aromatic hydrocarbon ring residue having 6 to 14 carbon atoms and a lower alkylene having 1 to 4 carbon atoms, (B) heterocyclic-alkyl resulting from binding of an aromatic heterocylic ring residue and a lower alkyl group having 1 to 4 carbon atoms, in which the aromatic heterocyclic ring is selected from the group consisting of 2-pyridyl, 3-pyridyl, 4-pyridyl, 2-pyrimidinyl, 4-pyrimidinyl, 5-pyrimnidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol-4-yl, tetrazol-5-yl, benzimidazol-2-yl, indol-3-yl, 1H-indazolyl, benz[b]furanyl, isobenzofuranyl, benz[b]thienyl, 1H-pyrrolo[2,3-b]pyradin-2-yl, 1H-pyrrolo[2,3-b]pyridin-6-yl, 1H-imidazo[4,5-p]pyridin-2-yl, 1H-imidazol[4,5-c]pyridin-2-yl and 1H-imidazo[4,5-b]pyrazin-2-yl or (C) linear or branched $C_{1-6}$ alkyl group which may have 1 to 3 substituents, at any position, selected from the group consisting of (i) linear or branched aliphatic hydrocarbon groups selected from the group consisting of $C_{1-10}$ alkyl groups, $C_{1-10}$ alkenyl groups and $C_{2-6}$ alkynyl groups, (ii) saturated or unsaturated alicyclic hydrocarbon groups selected from the group consisting of cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decy, 2-cyclopente-1-yl, 3-cyclopenten-1-yl, 2-cyclohexen-1-yl, 3-cyclohexen-1-yl, 2,4-cyclopentadien-1-yl, 2,4-cyclohexadien-1-yl, and 2,5-cyclohexadien-1-yl, (iii) aryl groups selected from the group consisting of phenyl, naphthyl, anthryl, phenanthryl, acenaphthylenyl; (iv) aromatic monocyclic heterocyclic groups selected from the group consisting of furyl, thienyl, pyrrolyl, oxazoly, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups selected from the group consisting of benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinoly, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo [1,2-a]pyridyl, imidazo[1,5-a]pyridyl, imidazo[1,2-b] pyridazinyl, imidazo[1,2-a]pyrimidinyl, 1,2,4-triazolo [4,3-a]pyridyl and 1,2,4-triazolo[4,3-b]pyridazinyl, (v) halogens selected from the group consisting of fluorine, chlorine, bromine and iodine, (vi) a nitro group (vii) optionally substituted amino groups selected from the group consising of amino, methylamino, dimethylamino, ethylamino, diethylamino, dibutylamino, diallylamino, cyclohexylamino, phenylamino, N-methyl-N-phenylamino, acetylamino, propionylamino and benzoylamino, (viii) acyl groups selected from the group consisting of formyl, acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, (ix) a hydroxyl group, $C_{1-10}$ alkoxy groups, $C_{1-10}$ alkenyloxy groups, phenyl-$C_{1-4}$ alkyloxy groups, $C_{2-4}$ alkanoyloxy groups and aryloxy groups selected from the group consisting of phenoxy and 4-chlorophenoxy, (x) a thiol group, $C_{1-10}$ alkylthio groups, phenyl-$C_{1-4}$ alkylthio groups and $C_{2-4}$ alkanoylthio groups, and (xi) optionally esterified carboxyl groups selected from the group consisting of carboxy, those resulting from binding of a carboxyl group and a $C_{1-6}$ alkyl group, those resulting from binding of a carboxyl group and a $C_{3-6}$ alkenyl group, benzyloxycarbonyl and phenetyloxycarbonyl;

$R^2$ and $R^3$ independently are a hydrogen atom or (A) an arylalkyl group resulting from binding of an aromatic hydrocarbon ring residue having 6 to 14 carbon atoms and a lower $C_{1-4}$ alkylene group which may have 1 to 3 substituents selected from the group consisting of (i) linear or branched aliphatic hydrocarbon groups selected from the group consisting of $C_{1-10}$ akyl groups, $C_{2-10}$ alkenyl groups and $C_{2-6}$ alkynyl groups, (ii) saturated or unsaturated alicyclic hydrocarbon groups selected from the group consisting of cyclopropyl, cyclobutyl, cyclopentyl, cyclohexyl, cycloheptyl, cycloctyl, bicyclo[2.2.1]heptyl, bicyclo[2.2.2] octyl, bicyclo[3.2.1]octyl, bicyclo[3.2.2]nonyl, bicyclo [3.3.1]nonyl, bicyclo[4.2.1]nonyl, bicyclo[4.3.1]decyl, 2-cyclopenten-1-yl, 3-cyclopenten-1-yl, 2cyclohexen1-yl, 3-cyclohexen-1-yl, 2,4-cyclopentadien-1-yl, 2,4-cyclohexadien-1 -yl and 2,5-cyclohexadien-1-yl, (iii) aryl groups selected from the group consisting of phenyl, naphthyl, anthryl, phenanthryl, acenaphthylenyl, (iv) aromatic monocyclic heterocyclic groups selected from the group consisting of furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups selected from the group consisting of benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrohnyl, indolizinyl, pyrrolo[1,2-b]pyridazinyl, pyrazolo[1,5-a]pyridyl, imidazo [1,2-a]pyridyl, imidazo[1,5-a]pyridyl, imidazo[1,2-b] pyridazinyl, imidazo[1,2a-]pyrimidinyl, 1,2,4-triazolo[4,3-a]pyridyl and 1,2,4-triazolo[4,3-b]pyridazinyl, (v) halogens selected from the group consisting of fluorine, chlorine, bromine and iodine, (vi) a nitro group, (vii) optionally substituted amino groups selected from the group consisting of amino, methylamino, dimethylamino, ethylamino, diethylamino, dibutylamino, diallylamino, cyclohexylamino, phenylamino, N-methyl-N-phenylamino, acetylamino, propionylamino and benzoylamino, (viii) acyl groups selected from the group consisting of formyl, acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexanecarbonyl,, benzoyl, nicotinoyl, (ix) a hydroxyl group, $C_{1-10}$ alkoxy groups, $C_{1-10}$ alkenyloxy groups, phenyl-$C_{1-4}$ alkyloxy groups, $C_{2-4}$ alkanoyloxy groups and aryloxy groups selected from the group consisting of phenoxy and 4-chlorophenoxy, (x) a thiol group, $C_{1-10}$ alkylthio groups, phenyl-$C_{1-4}$ alkylthio groups and $C_{2-4}$ alkanoylthio groups, and (xi) optionally esterified carboxyl groups selected from the group consisting of carboxy, those resulting from binding of a carboxyl group and a $C_{1-6}$ alkyl group, those resulting from binding of a carboxyl group, $C_{3-6}$ alkenyl group, benzyloxycarbonyl and phenetyloxycarbonyl or (B) a hydrocarbon group selected from the group consisting of linear or branched saturated aliphatic hydrocarbon residues having 1 to 8 carbon atoms, unsaturated aliphatic hydrocarbon residues having 2 to 8 carbon atoms, saturated alicyclic hydrocarbon residues having 3 to 7 carbon atoms, unsaturated alicyclic hydrocarbon residues having 5 to 7 carbon atoms and groups resulting from binding of (a) a saturated alicyclic hydrocarbon residue having 3 to 7 carbon atoms or an unsaturated alicyclic hydrocarbon residue having 5 to 7 carbon atoms and (b) a saturated aliphatic hydrocarbon residue having 4 to 9 carbon atoms, which hydrocarbon group may have 1 to 3 substituents selected from the group consisting of (i) halogens selected from the group consisting of fluorine, chlorine, bromine and iodine, (ii) nitro, (iii) optionally substituted amino groups selected from the group consisting of amino, methylamino, dimethylamino, ethylamino, diethylarnino, dibutylamino, diallylamino, cyclohexylarnino, phenylamino, N-methyl-N-phenylamino, acetylamino, propionylamino and benzoylamino, (iv) acyl groups selected from the group consisting of formyl, acetyl, propionyl, butyryl, isobutyiyl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, (v) a hydroxyl group, $C_{1-10}$ alkoxy groups, $C_{1-10}$ alkenyloxy groups, phenyl-$C_{1-4}$ alkyloxy groups, $C_{2-4}$ alkanoyloxy groups and aryloxy groups selected from the group consisting of phenoxy and 4-chlorophenoxy, (vi) a thiol group, $C_{1-10}$ alkylthio groups, phenyl-$C_{1-4}$ alkylthio groups and $C_{2-4}$ alkanoylthio groups and (vii) optionally esterified carboxyl groups selected from-the group consisting of carboxy, those resulting from binding of a carboxyl, group and a $C_{1-6}$ alkyl group, those resulting from binding of a carboxyl group and a $C_{3-6}$ alkenyl group, benzyloxycarbonyl and phenetyloxycarbonyl;

$R^4$ is
(1) a $C_{2-6}$ alkanoyl group substituted by $C_{9-12}$ aryl, or (2) a sulfonyl group, a carbamoyl group or a thiocarbamoyl group, each of said groups being substituted by (i) aryl having more than 9 carbon atoms selected from the group consisting of naphthyl, anthryl, phenanthryl and acenaphthylenyl, or (ii) $C_{1-6}$ alkyl; X is formula —CHO or —CH$_2$OB (wherein B is a hydrogen atom or a protecting group of hydroxy group); m and n independently are an integer of 0 or 1; or a salt thereof.

19. The method according to claim 18 wherein $R^1$ is an indolyl-lower ($C_{1-4}$) alkyl.

20. The method according to method according to claim 18 wherein $R^1$ is a naphthyl-lower ($C_{1-4}$) alkyl.

21. The method according to claim 18 wherein $R^1$ is a phenyl-lower ($C_{1-4}$) alkyl.

22. The method according to claim 18 wherein $R^1$ is a hydrogen or lower ($C_{1-6}$) alkyl.

23. The method according to claim 18 wherein $R^2$ is a branched lower ($C_{1-10}$) alkyl.

24. The method according to claim 18 wherein $R^2$ is a phenyl-lower ($C_{1-4}$) alkyl.

25. The method according to claim 18 wherein $R^3$ is a branched lower ($C_{1-10}$)alkyl.

26. The method according to claim 18 wherein $R^3$ is a hydrogen.

27. The method according to claim 18 wherein X is —CHO or —CH$_2$OH.

28. The method according to claim 18 wherein m is 1 and n is 1.

29. The method according to claim 18 wherein m is 1 and n is 0.

30. The method according to claim 18 wherein m is 0 and n is 0.

31. The method according to claim 18 wherein $R^1$ is a lower ($C_{1-6}$) alkyl which may be substituted by indolyl; $R^2$ is a lower ($C_{1-10}$) alkyl; $R^4$ is a naphthylsulfonyl or dibenzylacetyl; X is —CHO or —CH$_2$OH; m is 0 or 1 and n is 0.

32. The method according to claim 18 which contains N-dibenzylacetyl-(L)-tryptophanal.

33. The method according to claim 18 which contains N-(1-naphthylsulfonyl)-(L)-isoleucyl-(L)-alaninal.

34. The method according to claim 18 which contains N-(1-naphthylsulfonyl)-(L)-isoleucyl-(L)-tryptophanol.

35. A method for inhibiting catheprin L in a mammal, comprising administering to said mammal an effective catheprin L inhibiting amount of a compound of the formula:

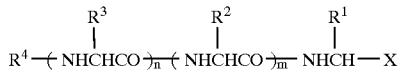

wherein $R^1$ is a hydrogen atom or (A) an arylakyl resulting from binding of an aromatic hydrocarbon ring residue having 6 to 14 carbon atoms and a lower alkylene having 1 to 4 carbon atoms, (B) heterocyclic-alkyl resulting from binding of an aromatic heterocylic ring residue and a lower alkyl group having 1 to 4 carbon atoms, in which the aromatic heterocyclic ring is selected from the group consisting of 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,2,3-triazol-4-yl, tetrazol-5-yl, benzimidazol-2-yl, indol-3-yl, 1H-indazolyl, benz[b]furanyl, isobenzofuranyl, benz[b]thienyl, 1H-pyrrolo[2,3-b]pyradin-2-yl, 1H-pyrrolo[2,3-b]pyridin-6-yl, 1H-imidazo[4,5-p]pyridin-2-yl, 1H-imidazol[4,5-c]pyridin-2-yl and 1H-imidazo[4,5-b]pyrazin-2-yl or (C) linear or branched $C_{1-6}$ alkyl group which may have 1 to 3 substituents, at any position, selected from the group consisting of (i) linear or branched aliphatic hydrocarbon groups selected from the group consisting of $C_{1-10}$ alkyl groups, $C_{2-10}$ alkenyl groups and $C_{2-6}$ alkynyl groups, (ii) saturated or unsaturated alicyclic hydrocarbon groups selected from the group consisting of cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decy, 2-cyclopenten-1-yl, 3-cyclopenten-1-yl, 2-cyclohexen-1-yl, 3-cyclohexen-1-yl,2,4-cyclopentadien1-yl, 2,4-cyclohexadien-1-yl and 2,5-cyclohexadien-1-yl, (iii) aryl groups selected from the group consisting of phenyl, naphthyl, anthryl, phenanthryl, acenaphthylenyl, (iv) aromatic monocyclic heterocyclic groups selected from the group consisting of furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups selected from the group consisting of benzofuranyl, isobenzofuranyl, benzo[b]thienyl, indolyl, isoindolyl, 1H-indazolyl, benzirnidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl, (v) halogens selected from the group consisting of fluorine, chlorine, bromine and iodine, (vi) a nitro group, (vii) optionally substituted amino groups selected from the group consisting of amino, methylamino, dimethylamino, ethylamino, diethylamino, dibutylamino, diallylamino, cyclohexylamino, phenylamino, N-methyl-N-phenylamino, acetylamino, propionylamino and benzoylamino, (viii) acyl groups selected from the group consisting of formyl, acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, (ix) a hydroxyl group, $C_{1-10}$ alkoxy groups, $C_{1-10}$ alkenyloxy groups, phenyl-$C_{1-4}$ alkyloxy groups, $C_{2-4}$ alkanoyloxy groups and aryloxy groups selected from the group consisting of phenoxy and 4-chlorophenoxy, (x) a thiol group, $C_{1-10}$ alkylthio groups, phenyl-$C_{1-4}$ alkylthio groups and $C_{2-4}$ alkanoylthio groups, and (xi) optionally esterified carboxyl groups selected from the group consisting of carboxy, those resulting from binding of a carboxyl group and a $C_{1-6}$ alkyl group, those resulting from binding of a carboxyl group and a $C_{3-6}$ alkenyl group, benzyloxycarbonyl and phenetyloxycarbonyl;

$R^2$ and $R^3$ independently are a hydrogen atom or (A) an arylalkyl group resulting from binding of an aromatic hydrocarbon ring residue having 6 to 14 carbon atoms and a lower $C_{1-4}$ alkylene group which may have 1 to 3 substituents selected from the group consisting of (i) linear or branched aliphatic hydrocarbon groups selected from the group consisting of $C_{1-10}$ alkyl groups, $C_{2-10}$ alkenyl groups and $C_{2-6}$ alkynyl groups, (ii) saturated or unsaturated alicyclic hydrocarbon groups selected from the group consisting of cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo

[3.3.1]nonyl, bicyclo[4.2.1]nonyl, bicyclo[4.3.1]decyl, 2-cyclopenten-1-yl, 3-cyclopenten-1-yl, 2-cyclohexen-1-yl, 3-cyclohexen-1-yl, 2,4-cyclopentadien-1-yl, 2,4-cyclohexadien-1-yl and 2,5-cyclohexadien-1-yl, (iii) aryl groups selected from the group consisting of phenyl, naphthyl, anthryl, phenanthryl, acenaphthylenyl, (iv) aromatic monocyclic heterocyclic groups selected from the group consisting of furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl and triazinyl, and aromatic condensed heterocyclic groups selected from the group consisting of benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxthinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b] pyridazinyl, imidazo[1,2-a]pyrimidinyl 1,2,4-triazolo[4,3-a] pyridyl and 1,2,4-triazolo[4,3-b]pyridazinyl, (v) halogens selected from the group consisting of fluorine, chlorine, bromine and iodine, (vi) a nitro group, (vii) optionally substituted amino group selected from the group consisting of amino, methylamino, dimethylamino, ethylamino, diethylamino, dibutylamino, diallylamino, cyclohexylamino, phenylamino, N-methyl-N-phenylamino, acetylamino, propionylamino and benzoylamino, (viii) acyl groups selected from the group consisting of formyl, acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, (ix) a hydroxyl group, $C_{1-10}$ alkoxy groups, $C_{1-10}$ alkenyloxy groups, phenyl-$C_{1-4}$ alkyloxy groups, $C_{2-4}$ alkanoyloxy groups and aryloxy groups selected from the group consisting of phenoxy and 4-chlorophenoxy, (x) a thiol group, $C_{1-10}$-alkylthio groups, phenyl-$C_{1-4}$ alkylthio groups and $C_{2-4}$ alkanoylthio groups, and (xi) optionally esterified carboxyl groups selected from the group consisting of carboxy, those resulting from binding of a carboxyl group and a $C_{1-6}$ alkyl group, those resulting from binding of a carboxyl group and a $C_{3-6}$ alkenyl group, benzyloxycarbonyl and phenetyloxycarbonyl or (B) a hydrocarbon group selected from the group consisting of linear or branched saturated aliphatic hydrocarbon residues having 1 to 8 carbon atoms, unsaturated aliphatic hydrocarbon residues having 2 to 8 carbon atoms, saturated alicyclic hydrocarbon residues having 3 to 7 carbon atoms, unsaturated alicyclic hydrocarbon residues having 5 to 7 carbon atoms and groups resulting from binding of (a) a saturated alicyclic hydrocarbon residue having 3 to 7 carbon atoms or an unsaturated alicyclic hydrocarbon residue having 5 to 7 carbon atoms and (b) a saturated aliphatic hydrocarbon residue having 4 to 9 carbon atoms, which hydrocarbon group may have 1 to 3 substituents selected from the group consisting of (i) halogens selected from the group consisting of fluorine, chlorine, bromine and iodine, (ii) nitro, (iii) optionally substituted amino groups selected from the group consisting of amino, methylamino, dimethylamino, ethylamino, diethylamino, dibutylamino, diallylamino, cyclohexylamino, phenylamino, N-methyl-N-phenylamino, acetylamino, propionylamino and benzocylamino, (iv) acyl groups selected from the group consisting of formyl, acetyl, propionyl, butyryl, isobutyryl, valeryl, isovaleryl, pivaloyl, hexanoyl, heptanoyl, octanoyl, cyclobutanoyl, cyclopentanoyl, cyclohexanoyl, cycloheptanoyl, crotonyl, 2-cyclohexenecarbonyl, benzoyl, nicotinoyl, (v) a hydroxyl group, $C_{1-10}$ alkoxy groups, $C_{1-10}$ alkenyloxy groups, phenyl-$C_{1-4}$ alkyloxy groups, $C_{2-4}$ alkanoyloxy groups and aryloxy groups selected from the group consisting of phenoxy and 4-chlorophenoxy, (vi) a thiol group, $C_{1-10}$ alkylthio groups, phenyl-$C_{1-4}$ alkylthio groups and $C_{2-4}$ alkanoylthio groups, and (vii) optionally esterified carboxyl groups selected from the group consisting of carboxy, those resulting from binding of a carboxyl group and a $C_{1-6}$ alkyl group, those resulting from binding of a carboxyl group and a $C_{3-6}$ alkenyl group, benzyloxycarbonyl and phenetyloxycarbonyl;

$R^4$ is:

(1) a $C_{2-6}$ alkanoyl group substituted by $C_{9-12}$ aryl, or (2) a sulfonyl group, a carbamoyl group or a thiocarbamoyl group, each of said groups being substituted by (i) aryl having more than 9 carbon atoms selected from the group consisting of naphthyl, anthryl, phenanthryl and acenaphthylenyl, or (ii) $C_{1-6}$ alkyl;

X is formula —CHO or —CH$_2$OB (wherein B is a hydrogen atom or a protacting group of hydroxy group); m and n independently are an integer of 0 or 1; or a salt thereof.

36. The method according to claim 35 wherein $R^1$ is an indolyl-lower ($C_{1-4}$) alkyl.

37. The method according to method according to claim 35 wherein $R^1$ is a naphthyl-lower ($C_{1-4}$) alkyl.

38. The method according to claim 35 wherein $R^1$ is a phenyl-lower ($C_{1-4}$) alkyl.

39. The method according to claim 35 wherein $R^1$ is a hydrogen or lower ($C_{1-6}$) alkyl.

40. The method according to claim 35 wherein $R^2$ is a branched lower ($C_{1-10}$) alkyl.

41. The method according to claim 35 wherein $R^2$ is a phenyl-lower ($C_{1-4}$) alkyl.

42. The method according to claim 35 wherein $R^3$ is a branched lower ($C_{1-10}$).

43. The method according to claim 35 wherein $R^3$ is a hydrogen.

44. The method according to claim 35 wherein X is —CHO or —CH$_2$OH.

45. The method according to claim 35 wherein m is 1 and n is 1.

46. The method according to claim 35 wherein m is 1 and n is 0.

47. The method according to claim 35 wherein m is 0 and n is 0.

48. The method according to claim 35 wherein $R^1$ is a lower ($C_{1-6}$) alkyl which may be substituted by indolyl; $R^2$ is a lower ($C_{1-10}$) alkyl; $R^4$ is a naphthylsulfonyl or dibenzylacetyl; X is —CHO or —CH$_2$OH; m is 0 or 1 and n is 0.

49. The method according to claim 35, which contains N-dibenzylacetyl-(L)-tryptophanal.

50. The method according to claim 35, which contains N-(1naphthylsulfonyl)-(L)-isoleucyl-(L)-alaninal.

51. The method according to claim 35, which contains N-(1naphthylsulfonyl)-(L)-isoleucyl-(L)-tryptophanol.

* * * * *